(12) United States Patent
Song et al.

(10) Patent No.: US 11,357,887 B2
(45) Date of Patent: Jun. 14, 2022

(54) DELIVERY SYSTEMS BASED ON HYDROGEL COMPOSITIONS AND METHODS THEREOF

(71) Applicant: University of Massachusetts, Boston, MA (US)

(72) Inventors: Jie Song, Shrewsbury, MA (US); Yu Tan, Worcester, MA (US); Henry Huang, Somerville, MA (US)

(73) Assignee: University of Massachusetts, Boston, MA (US)

( * ) Notice: Subject to any disclaimer, the term of this patent is extended or adjusted under 35 U.S.C. 154(b) by 59 days.

(21) Appl. No.: 16/756,455

(22) PCT Filed: Nov. 11, 2018

(86) PCT No.: PCT/US2018/060236
§ 371 (c)(1),
(2) Date: Apr. 15, 2020

(87) PCT Pub. No.: WO2019/094852
PCT Pub. Date: May 16, 2019

(65) Prior Publication Data
US 2020/0261616 A1   Aug. 20, 2020

Related U.S. Application Data

(60) Provisional application No. 62/584,402, filed on Nov. 10, 2017.

(51) Int. Cl.
*A61L 27/18* (2006.01)
*A61L 27/52* (2006.01)
*A61L 27/54* (2006.01)
*C08L 71/02* (2006.01)

(52) U.S. Cl.
CPC ............... *A61L 27/18* (2013.01); *A61L 27/52* (2013.01); *A61L 27/54* (2013.01); *A61L 2400/06* (2013.01); *C08L 71/02* (2013.01)

(58) Field of Classification Search
CPC .......... A61L 27/18; A61L 27/52; A61L 27/54; A61L 2400/06; C08L 71/02
See application file for complete search history.

(56) References Cited

U.S. PATENT DOCUMENTS

2017/0182220 A1*   6/2017   Song .................... A61L 27/18

OTHER PUBLICATIONS

PCT/US18/60236, Int'l Search Report and Written Opinion of the ISA, 2019.
Chaudhuri et al. "Hydrogels with tunable stress relaxation regulate stem cell fate and activity" Nature Materials, vol. 15, 326-334 (2016).

* cited by examiner

*Primary Examiner* — Shirley V Gembeh
(74) *Attorney, Agent, or Firm* — Milstein Zhang & Wu LLC

(57) ABSTRACT

The invention provides a novel, versatile degradable hydrogel composition, and methods thereof, with precisely tunable stiffness, plasticity (e.g., degree of covalent vs. physical crosslinks) and predictive disintegration rates degradation, allowing controlled disintegration and release of therapeutic cells or pharmaceuticals and/or in vitro 3D cell expansion.

14 Claims, 11 Drawing Sheets

DELIVERY SYSTEMS BASED ON HYDROGEL COMPOSITIONS AND METHODS THEREOF

PRIORITY CLAIMS AND RELATED APPLICATIONS

This application is the U.S. national phase of and claims priority to PCT/US18/60236, filed Nov. 11, 2018, which claims the benefit of priority from U.S. Provisional Application Ser. No. 62/584,402, filed on Nov. 10, 2017, the entire content of each of which is incorporated herein by reference.

TECHNICAL FIELD OF THE INVENTION

The invention generally relates to hydrogels and delivery of therapeutics. More particularly, the invention relates to a novel, versatile degradable hydrogel composition, and methods thereof, having precisely tunable stiffness, plasticity and degradation, allowing controlled disintegration and release of therapeutic cells or pharmaceuticals.

BACKGROUND OF THE INVENTION

Hydrogels have been used to encapsulate and deliver stem cells or primary cells to promote tissue regeneration. Hydrogel with controlled degradation behaviors are especially useful for a variety of biomedical applications (e.g., drug delivery and tissue regeneration). It is increasingly appreciated that hydrogel stiffness, matrix plasticity/viscoelasticity and degradation modulate cell-hydrogel interactions and consequently cellular behaviors including proliferation, morphogenesis, differentiation/phenotypical matrix deposition. (Diekjurgen, et al. 2017 *Biomaterials* 141, 96; Shin, et al. 2016 *Proc. Natl. Acad. Sci. U.S.A* 113 (43), 12126; Yang, et al. 2014 *Nature materials* 13 (6), 645; Khetan, et al. 2013 *Nature materials* 12 (5), 458.)

Natural polymer-based hydrogels such as Matrigel™ and a range of polysaccharide-based hydrogels such as alginate have been exploited for cell encapsulations due to their cytocompatibility. Recent studies demonstrated the impact of viscoelasticity of alginate-based hydrogels on the cellular behavior of encapsulated mesenchymal stem cells (MSCs) by modulating the molecular weight of alginate, the degree of $Ca^{2+}$-induced physical crosslinking, and the introduction of covalently tethered poly(ethylene glycol) chains. Viscoelasticity of natural hydrogels, imposed by extensive physical interactions within the polymer network, has been recognized as critical for alleviating the elastic stress of hydrogel matrix to encapsulated cells. (Diekjurgen, et al. 2017 *Biomaterials* 141, 96; Chaudhuri, et al. 2016 *Nature materials* 15 (3), 326.)

Difficulty in achieving regiospecific and stoichiometrically controlled chemical modification of natural polymers limits tunability of their biophysical and degradative properties. This limitation, combined with batch-to-batch variation in their matrix compositions, residue animal-derived components, and risks for contamination/immunogenicity, presents significant hurdles to their regulatory approval and clinical translation.

Unlike natural biopolymer-based hydrogels, wholly synthetic hydrogels can be prepared free of biocontaminants. The use of wholly synthetic hydrogels for cell encapsulation, however, has been largely limited to investigating the impact of stiffness of photo-crosslinked polymethacrylate-based hydrogels on the cellular fate of MSCs or the matrix deposition of encapsulated chondrocytes in vitro. Modulation of stiffness of these hydrogels was mainly accomplished by altering degree of covalent crosslinking or polymer weight fractions, which did not address the negative impact of high elastic stress imposed by these hydrogel networks to the metabolism of encapsulated cells. (Benoit, et al. 2008 *Nature materials* 7 (10), 816; Lutolf, et al. 2005 *Nat. Biotechnol.* 23 (1), 47; Mao, et al. 2016 *Biomaterials* 98, 184; Engler, et al. 2006 *Cell* 126 (4), 677; Butler, et al. 2009 *Tissue engineering. Part B, Reviews* 15 (4), 477; Bryant, et al. 2004 *J. Orthop. Res.* 22 (5), 1143.)

In addition, the radical initiators and photo-irradiation employed to covalently crosslink these hydrogels are known for imposing cytotoxicity/altering gene expression of encapsulated cells. Meanwhile, covalent incorporation of degradable polylactide segments has been utilized to introduce degradability to elastic covalently crosslinked hydrogel network to promote encapsulated cell matrix deposition and/or to enable cell release. Such a method of modulating hydrogel degradability, however, is empirical rather than predictive in nature, and generates significant inflammatory acidic degradation products. (Gasparian, et al. 2015 *Anal. Biochem.* 484, 1; Fedorovich, et al. 2009 *Biomaterials* 30 (3), 344; Filion, et al. 2011 *Biomaterials* 32 (4), 985; Bergsma 1995 *Biomaterials* 16 (1), 25; Chu, et al. 2017 *Tissue Eng Part A* 23 (15-16), 795; Bryant, et al. 2003 *J. Biomed. Mater. Res. A* 64 (1), 70.)

Overall, it remains a significant challenge to develop a wholly synthetic 3D hydrogel where its matrix stiffness, plasticity and degradative property can be quantitatively and predictively tuned over a broad range for facile cell encapsulation, to accommodate cell proliferation/phenotypical matrix deposition, and to enable precisely timed release for in vivo cell delivery.

There is an urgent and ongoing need for novel and improved approaches that effectively address these issues.

SUMMARY OF THE INVENTION

The invention provides wholly synthetic hydrogels useful for cell encapsulation and delivery with predictive tuning of stiffness, plasticity/viscoelasticity and degradation of tissue matrices regulate cell behavior. In particular, disclosed is a novel 3D synthetic hydrogel platform with explicitly controlled ratio of biorthogonal covalent vs. non-covalent crosslinking of cytocompatible building blocks and strategic placement of a single stable vs. labile linker near the crosslinking site. The former dictates the matrix stiffness and viscoelasticity while the later predicts matrix degradation.

For example, hydrogels with varying stiffness (e.g., 0.86-11.75 KPa) and matrix plasticity (degree of covalent vs. physical crosslinks) and predictive disintegration rates (e.g., 18→150 days) were prepared from 2 pairs of labile/stable building blocks in varying ratios for 3D encapsulation of rodent and human chondrocytes. Stiffer hydrogels strengthened by dynamic physical crosslinks between dibenzocyclooctyne (DBCO)-terminated building blocks better absorbed the stress and accommodated the expanding volume imposed by the proliferation of and chondrogenic matrix deposition by encapsulated chondrocytes. Degradation of the hydrogel promoted the proliferation and matrix deposition of encapsulated chondrocytes, with those released upon timed gel disintegration maintaining their chondrogenic phenotype.

The present disclosure demonstrates that high-fidelity biorthogonal covalent and physical crosslinking of a small set of designer building blocks can be conveniently exploited to engineer 3D synthetic niches with tunable matrix stiffness, plasticity and predictive degradative properties for cell encapsulation, expansion and release In one aspect, the invention generally relates to a hydrogel comprising a 3-dimentional crosslinking network of a combination of covalent crosslinking (CX) and non-covalent crosslinking (NCX) of hydrophilic branched polymers,

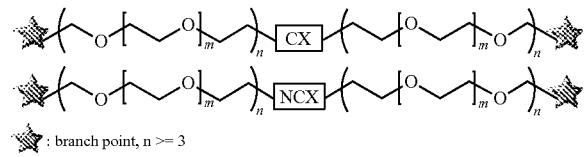

wherein the hydrophilic branched polymers are star-branched with at least 3 arms.

In another aspect, the invention generally relates to a hydrogel composition comprising a hydrogel disclosed herein and a biologically active payload encapsulated therein.

In yet another aspect, the invention generally relates to a device or implant that includes a hydrogel or a hydrogel composition disclosed herein.

In yet another aspect, the invention generally relates to a method for modulating one or more properties of a hydrogel. The method includes: incorporating in the hydrogel a 3-dimensional crosslinking network of a combination of covalent crosslinking (CX) and non-covalent crosslinking (NCX) of hydrophilic branched polymers,

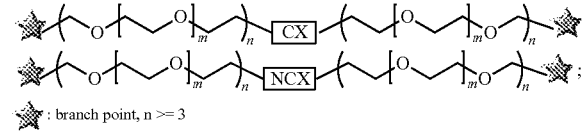

adjusting and/or controlling the ratio of covalent crosslinking (CX) to non-covalent crosslinking (NCX) of hydrophilic branched polymers; and adjusting and/or controlling the placement and ratio of one or more labile linkages to one or more stable linkages in the hydrophilic branched polymers. The hydrophilic branched polymers are star-branched with at least 3 arms. The property is one or more selected from viscoelasticity, stiffness and degradation.

In yet another aspect, the invention generally relates to a method for delivering a biologically active payload. The method includes: placing in a subject in need thereof a device or implant comprising a hydrogel or hydrogel composition disclosed herein, and causing a controlled release of the biologically active payload.

ns: p>0.05 (two-way ANOVA with Tukey's multiple comparisons vs. the 1:1 formulation at a given time).

Figure 6:
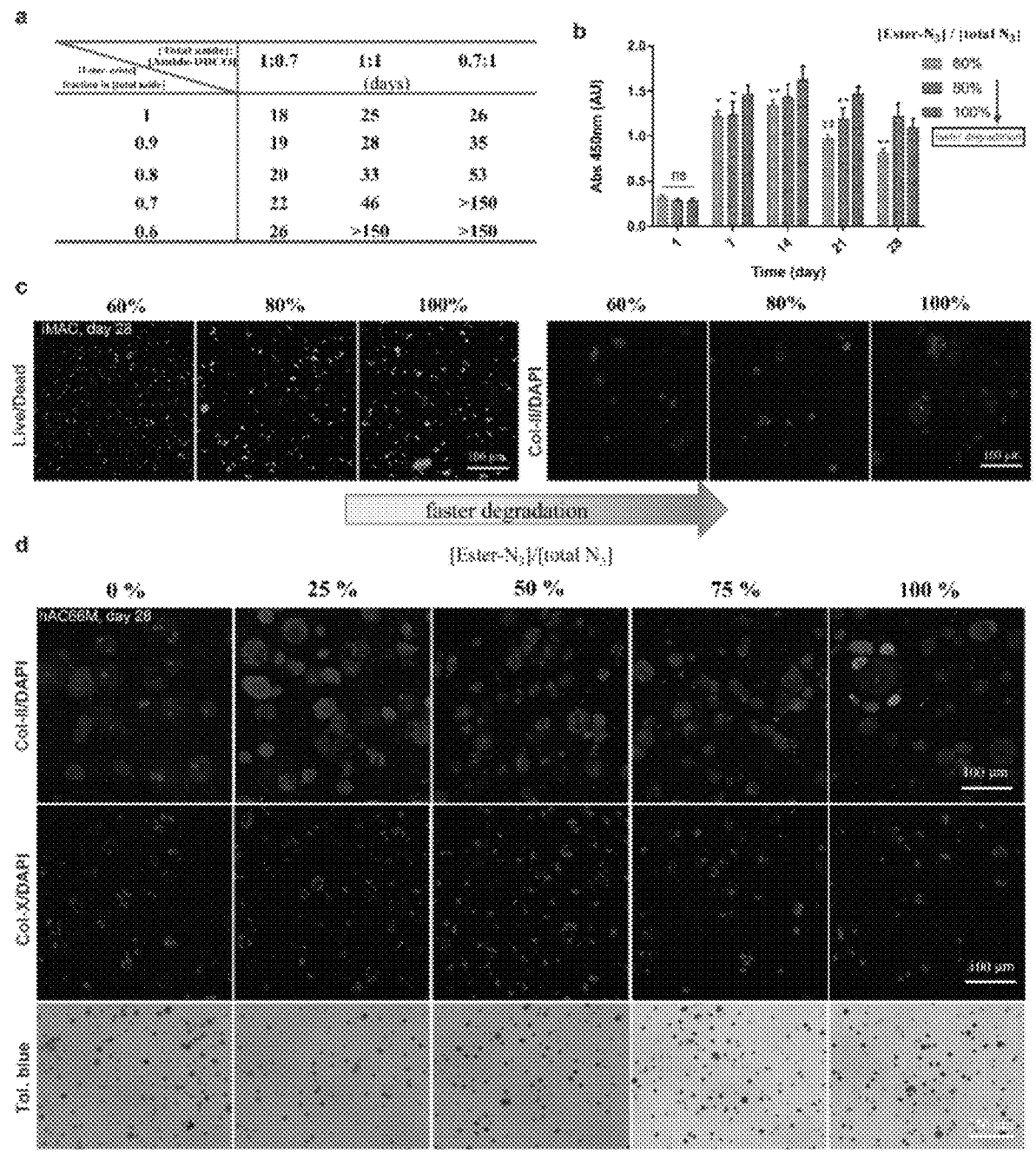

FIG. 6. ClickGel degradation enhances proliferation and chondrogenic ECM depositions of encapsulated iMACs and human chondrocytes. a. Disintegration time of ClickGels (5 w/v %) formed between non-labile DBCO-terminated macromer and a mixture of non-labile and labile azide-terminated macromers upon incubation in expansion media. b. Viability of iMACs encapsulated within perfectly SPAAC-crosslinked ClickGels with varying degradability (250,000/25-pt gel) in expansion media over time. c. Live (green)/dead (red) staining and type II collagen (green)/DAPI (blue) immunofluorescent staining of iMAC-laden ClickGels with varying degradability on day 28 of culture in expansion media. d. Type II collagen (green)/DAPI (blue), type X collagen (green)/DAPI (blue) immunofluorescent staining and toluidine blue (for GAG) staining of human chondrocyte-laden ClickGels with varying degradability in chondrogenic media. ns: $p>0.05$; *$p<0.05$; $p<0.01$; ***$p<0.0001$ (two-way ANOVA with Tukey's multiple comparisons vs. the 100% gel).

Figure 7:
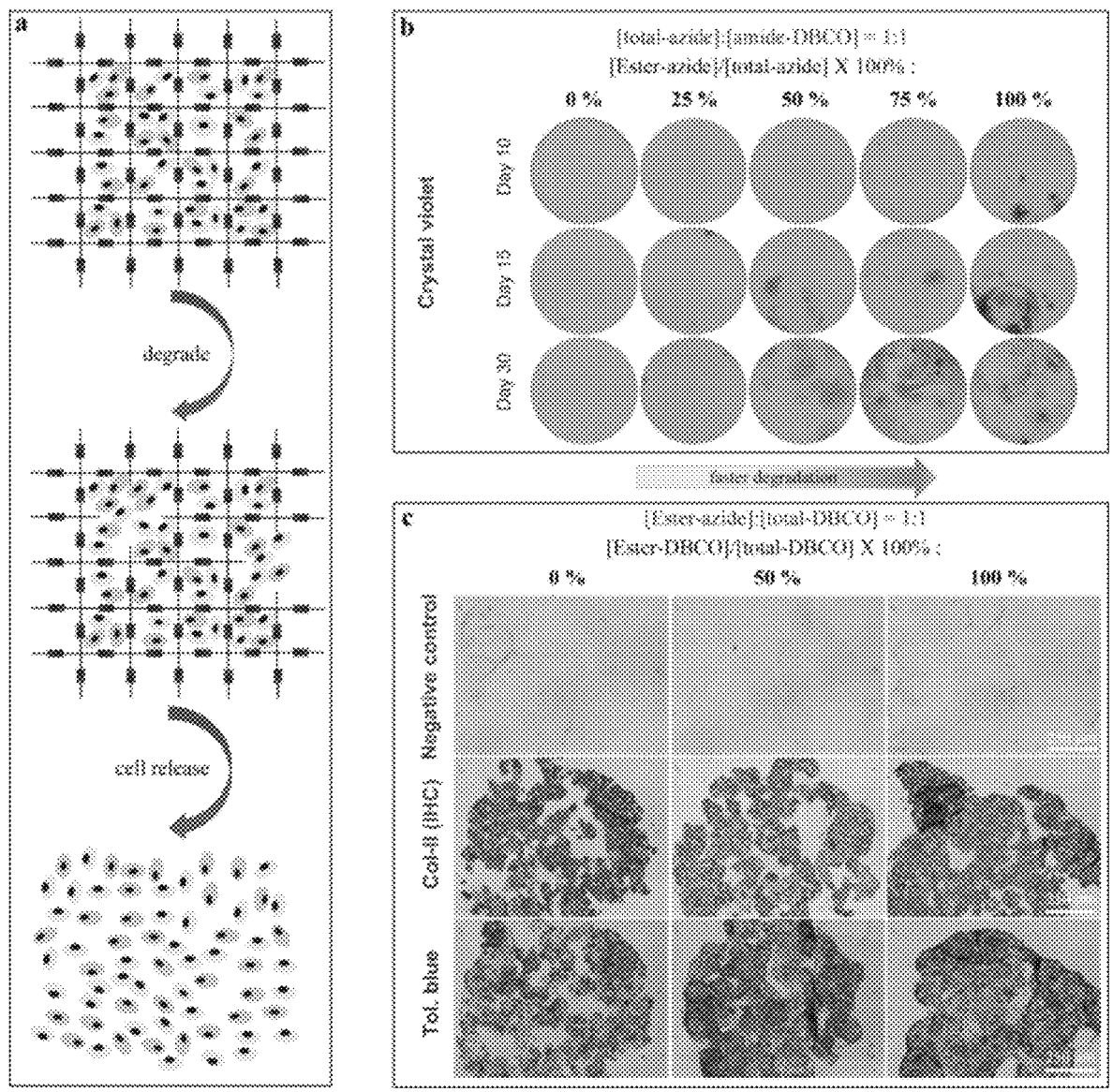

FIG. 7. Degradable ClickGels (5 w/v %, perfectly SPAAC-crosslinked) enable timed release of encapsulated iMACs with retained chondrogenic phenotype. a. Depiction of ClickGel network disintegration as a result of hydrolysis of labile SPAAC crosslinks and the release of encapsulated cells. b. Crystal violet staining of cells released from ClickGels with varying degradability over different culture duration in expansion media. c. GAG and type II collagen staining of the pellet of released iMACs. Upon complete disintegration of the degradable ClickGel, released iMAC were pelleted and cultured in expansion media for 10 days prior to staining.

Figure 8:
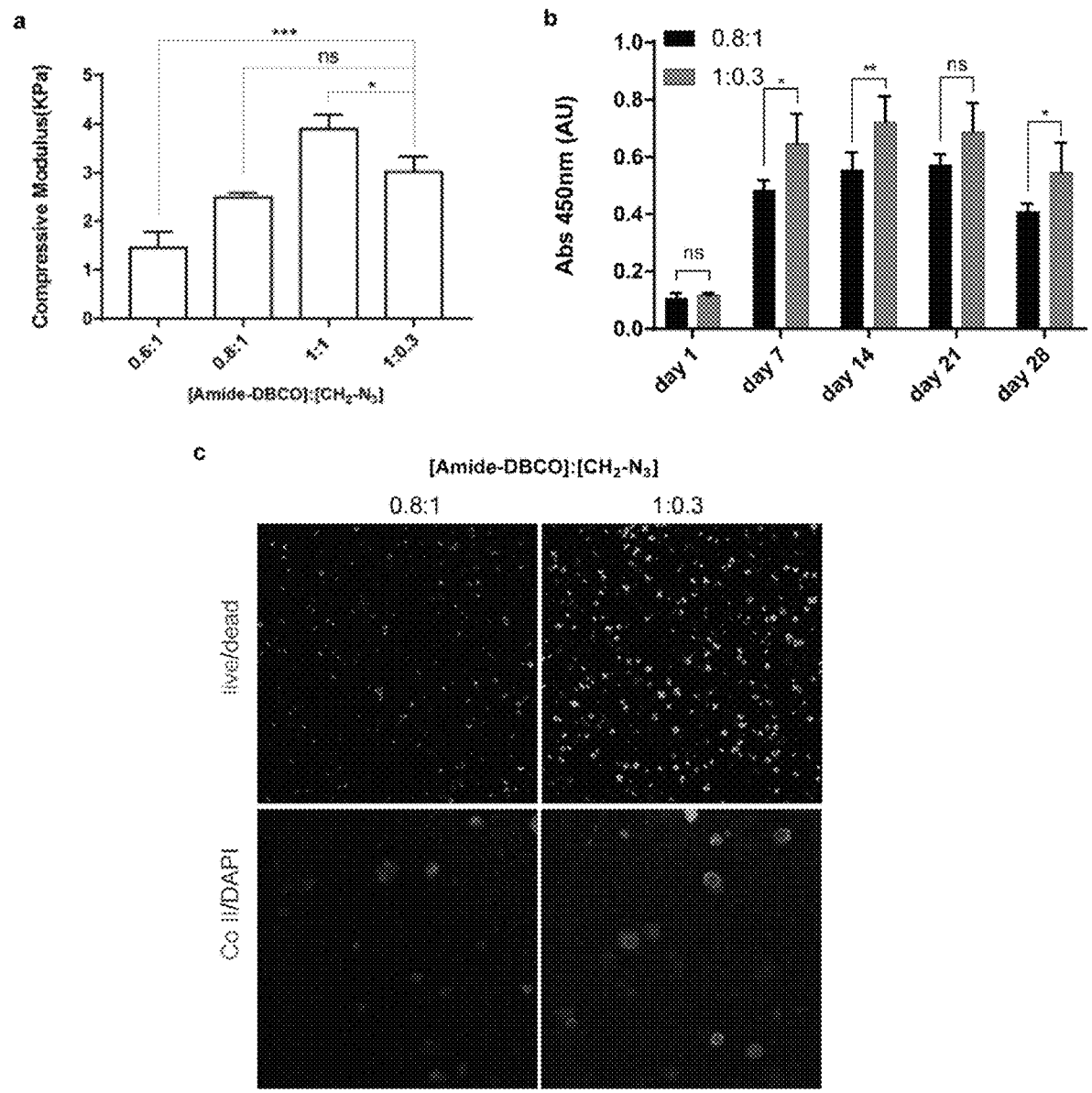

FIG. 8: Non-degradable ClickGels (5 w/v %) crosslinked between mismatched ratios of DBCO- and $N_3$-terminated macromers exhibit varying stiffness, with the ClickGel formed with only 30% covalent SPAAC crosslinks and 70% excess DBCO-terminated macromers exhibiting higher compressive moduli (0-30% strain), viability than matrix deposition than those formed with 60-80% covalent SPAAC crosslinks but excess $N_3$-terminated macromers. a. compressive moduli. b. Viability of encapsulated iMAC as a function of ClickGel composition over 28 days. c. Live (green)/dead (red) staining and type II collagen (green)/DAPI (blue) immunofluorescent staining of iMAC-laden ClickGels (0.8:1 vs 1:0.3) on day 28 of culture in expansion media. ns: $p>0.05$; *$p<0.05$; ***$p<0.001$ (one-way ANOVA with Dunnett's multiple comparisons or Sidak's multiple comparisons test vs. the 1:0.3 formulation).

Figure 9:
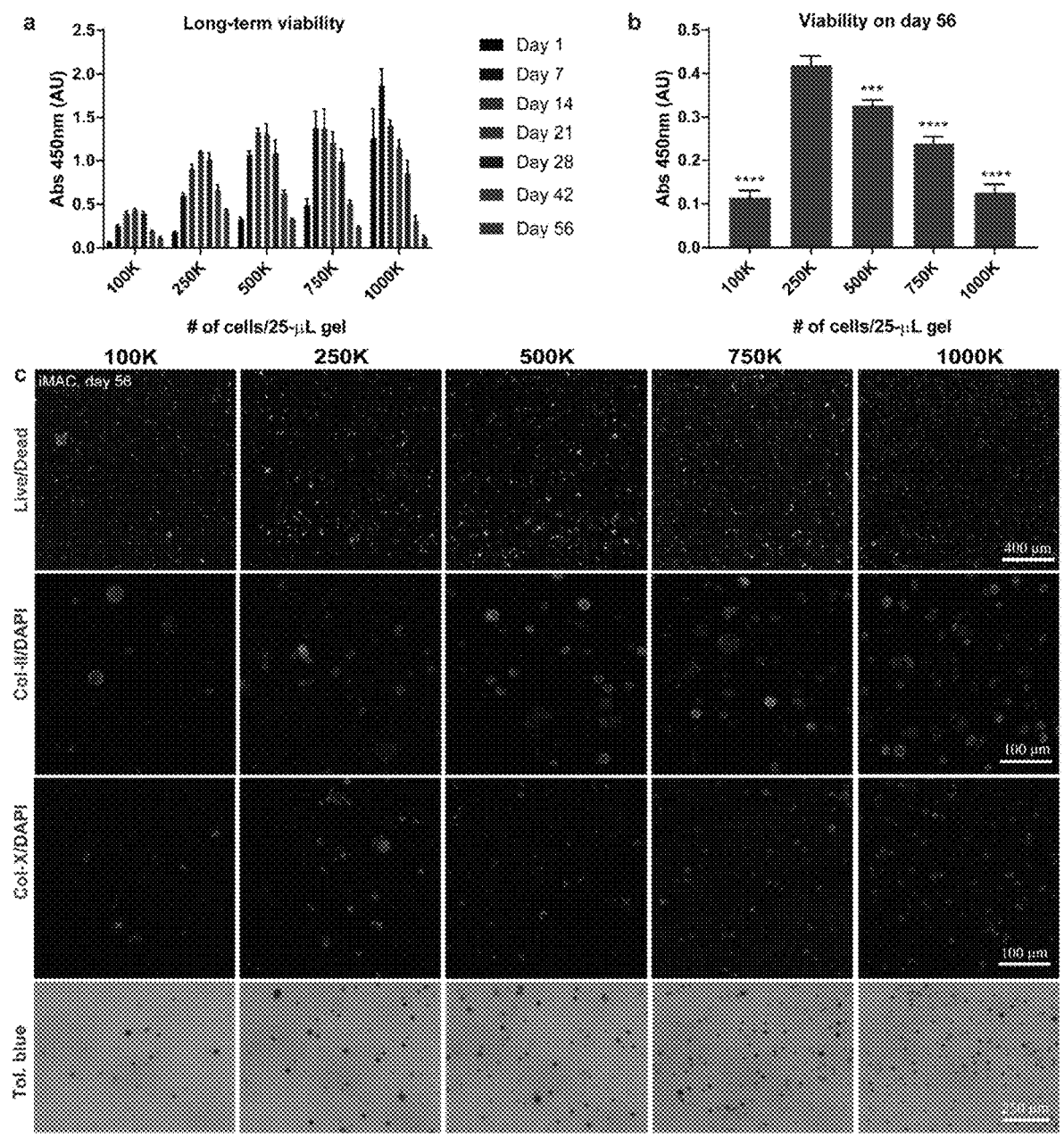

FIG. 9: iMACs proliferate and maintain chondrocyte phenotype in perfectly SPAAC-crosslinked non-degradable ClickGel while excessive initial cell encapsulation densities reduce long-term viability of iMACs. a. Viability of iMACs over time as a function of initial encapsulation density. b. Viability of iMACs on day 56 as a function of initial encapsulation density. c. Live (green)/dead (red) staining, type II collagen (green)/DAPI (blue) staining, type X collagen (green)/DAPI (blue) immunofluorescent staining and toluidine blue staining of iMAC-laden ClickGels with varying initial cell encapsulation densities after 56-day culture. 250,000-1,000,000 iMACs were encapsulated in 25-μL 5 wt % perfectly SPAAC-crosslinked non-degradable ClickGels and cultured in expansion media (high glucose DMEM supplemented with 10% FBS and 1% Pen/Strep). *$p<0.001$; ***$p<0.0001$ (one-way ANOVA with Tukey's multiple comparisons vs. the 250K cell encapsulation density).

Figure 10:
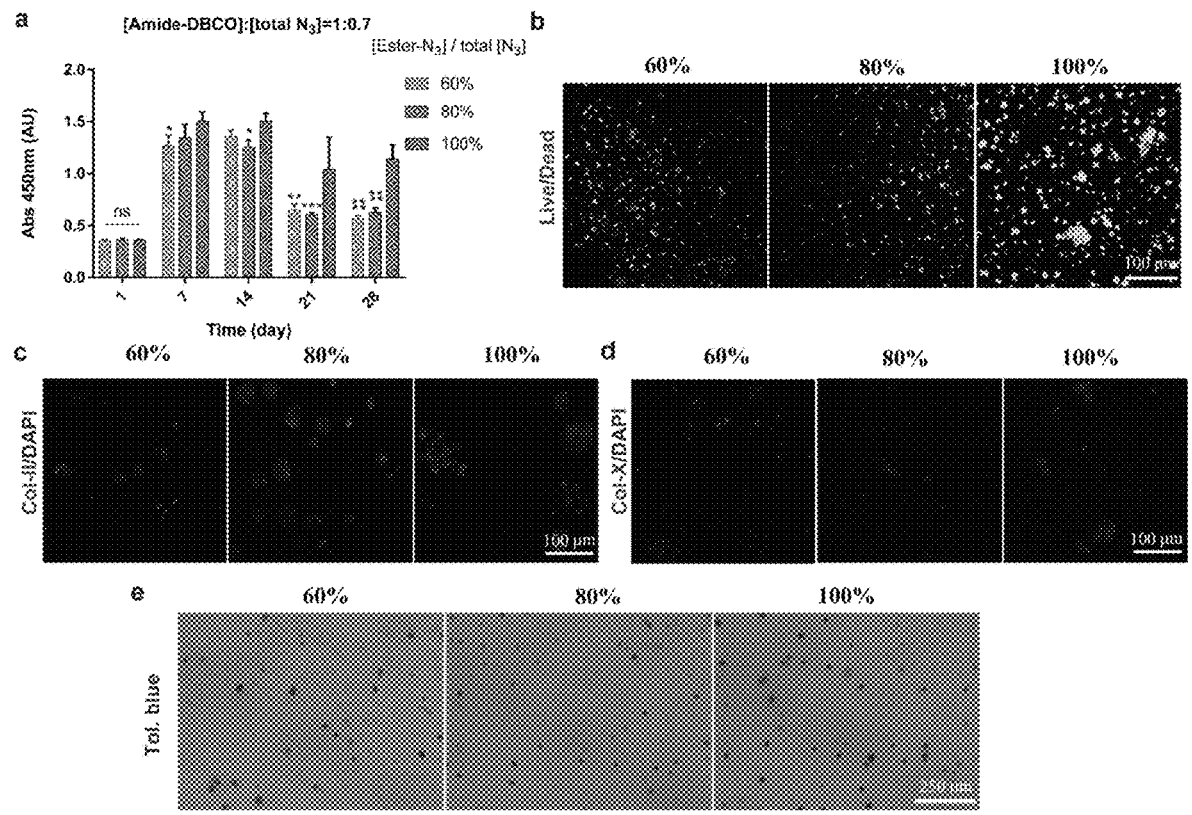

FIG. 10: ClickGel degradation enhances proliferation and chondrogenic ECM depositions of encapsulated iMACs in imperfect network a. Viability of iMACs encapsulated within perfectly SPAAC-crosslinked ClickGels with varying degradability (250,000/25 μL gel) in expansion media over time. b. Live (green)/dead (red) staining, c. type II collagen (green)/DAPI (blue) and d. type X collagen (green)/DAPI (blue) immunofluorescent staining of iMAC-laden ClickGels with varying degradability on day 28 of culture in expansion media. e. toluidine blue (for GAG) staining of human chondrocyte-laden ClickGels with varying degradability in chondrogenic media. ns: $p>0.05$; *$p<0.05$; $p<0.01$; ***$p<0.0001$ (two-way ANOVA with Tukey's multiple comparisons vs. the 100% gel).

Figure 11:
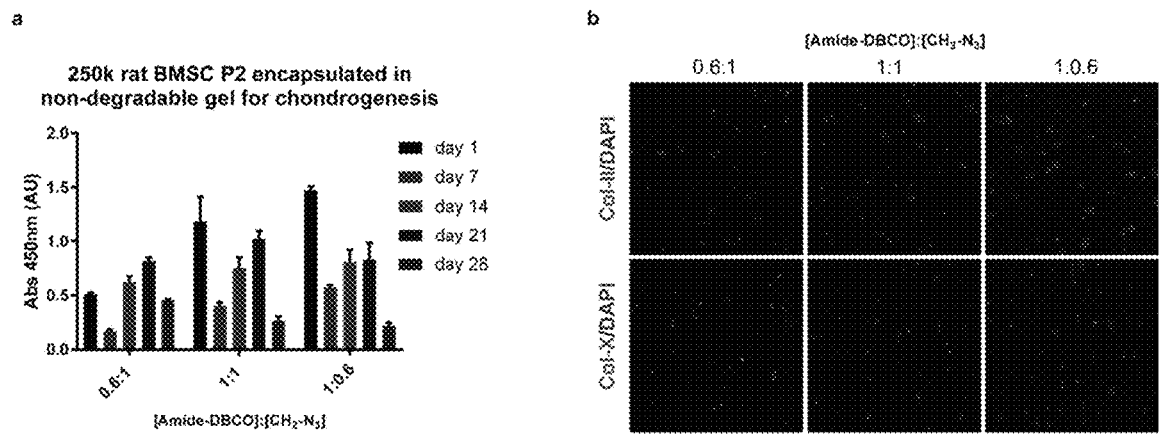

FIG. 11: Rat BMSC encapsulated in non-degradable ClickGels maintain viability and chondrocyte phenotype in chondrogenic culture. a. Viability of encapsulated rat BMSC as a function of ClickGel composition over 28 days. b. type II collagen (green)/DAPI (blue) and type X collagen (green)/DAPI (blue) immunofluorescent staining of rat BMSC-laden ClickGels of varying compositions on day 28 of chondrogenic culture. 250,000 rat BMSCs were encapsulated in 25-μL 5 wt % non-degradable ClickGels of varying macromer ratios and cultured in chondrogenic media.

DETAILED DESCRIPTION OF THE INVENTION

The invention provides a novel 3D synthetic hydrogel platform with explicitly controlled ratio of biorthogonal covalent vs. non-covalent crosslinking of cytocompatible building blocks and strategic placement of a single stable vs. labile linker near the crosslinking site. The wholly synthetic hydrogels disclosed herein are useful for cell encapsulation/delivery with predictive tuning of stiffness, plasticity/viscoelasticity and degradation of tissue matrices regulate cell behavior. In particular, covalent vs. non-covalent crosslinking cytocompatible building blocks regulators matrix stiffness and viscoelasticity while positioning of stable vs. labile linkers controls matrix degradation.

The disclosed synthetic hydrogel is characterized by a well-structured crosslinking network where the matrix stiffness and plasticity is dictated by tunable combinations of biorthogonal covalent and non-covalent physical crosslinking of cytocompatible building blocks while the degradation is predictively controlled by the strategic placement of isolated labile linkages near the crosslinking site. For example, strain-promoted alkyne-azide cycloaddition (SPAAC) can proceed efficiently in the absence of catalysts or irradiation under physiological conditions between reactants functionalized with azides and cyclooctynes, which are absent from native cellular/tissue environment. It has been utilized for the preparation of covalently crosslinked hydrogels for cell encapsulation. (Jewett, et al. 2010 *Chem. Soc. Rev.* 39 (4), 1272; Agard, et al. 2005 *J. Am. Chem. Soc.* 127 (31), 11196; Zheng, et al. 2012 *ACS macro letters* 1 (8), 1071; Caldwell, et al. 2017 *Advanced healthcare materials* 6 (15); Xu, et al. 2014 *J. Am. Chem. Soc.* 136 (11), 4105; Xu, et al. 2011 *Chem. Asian J.* 6 (10), 2730; DeForest, et al. 2009 *Nature materials* 8 (8), 659.)

It was recently demonstrated that by SPAAC-crosslinking 4-armed poly(ethylene glycol)-tetra-dibenzocyclooctyl (4-armPEG-DBCO) and 4-armed poly(ethylene glycol)-tetra-azide (4-armPEG-azide) with a single labile ester linkage (X=O; Y=OC(O)—C$_3$H$_6$) or stable (X=NH; Y=absent) linkage near the azide or DBCO group (FIG. 1, [DBCO]:[N$_3$]=1:1), cytocompatible hydrogels named ClickGels with gelling kinetics (2-5 min) suitable for cell encapsulation and predictive degradation over a broad range could be prepared. The strategic placement of a single labile ester linkage at either side of the SPAAC crosslink (distinct K$_d$'s for hydrolysis at X vs. Y site) within a well-structured hydrophilic network enabled prediction of the ClickGel disintegration based on 1$^{st}$-order hydrolytic cleavage kinetics. (Xu, et al. 2014 *J. Am. Chem. Soc.* 136 (11), 4105; Xu, et al. 2014 *J. Am. Chem. Soc.* 136 (11), 4105.)

While prospective tuning of the ClickGel disintegration rate from days to months, was accomplished, the challenge remained for controlled engineering of stiffness and matrix plasticity/viscoelasticity.

Figure 1:
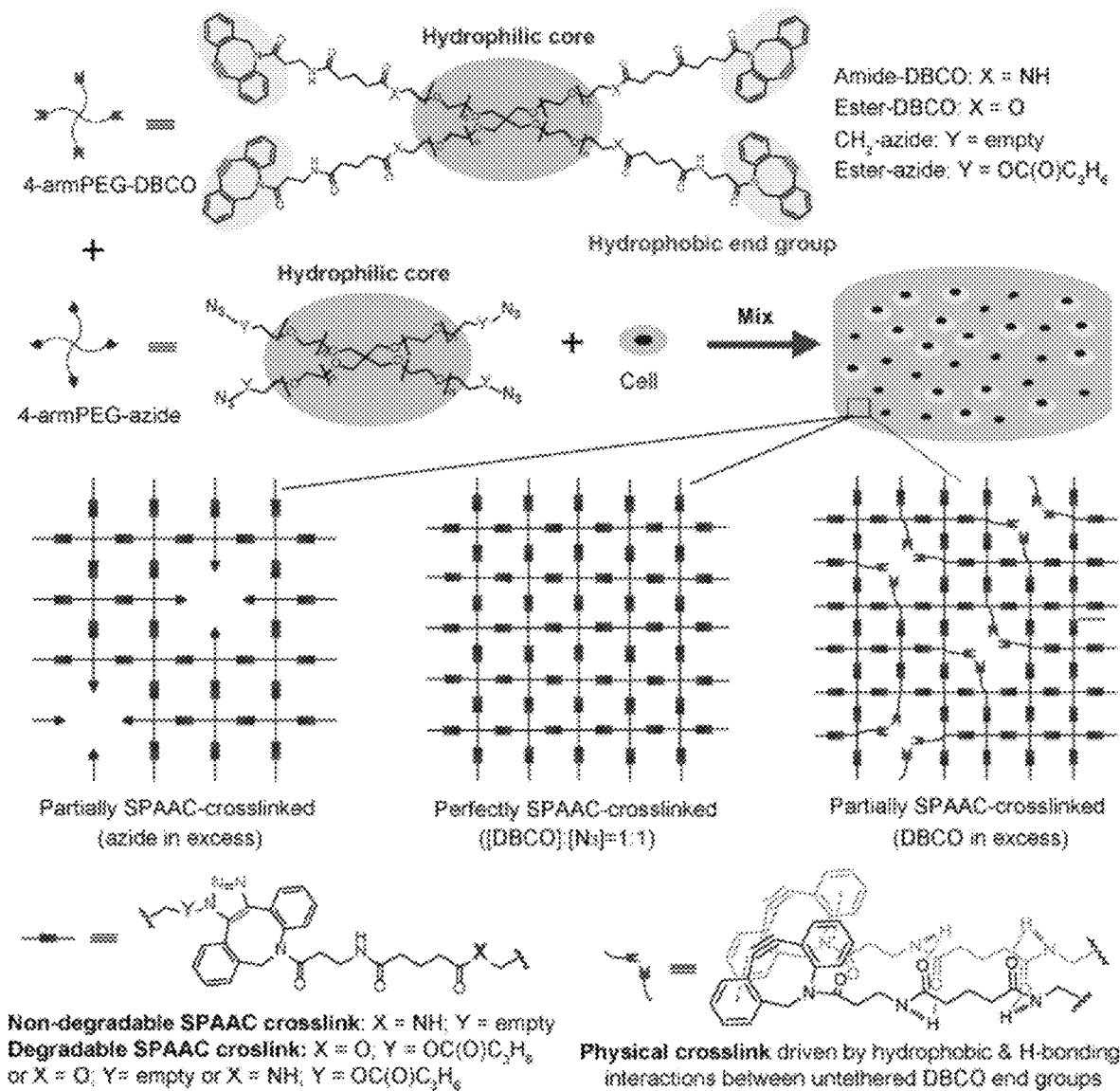
FIG. 1. Depiction of catalyst-free, irradiation-free encapsulation of cells by ClickGels with varying degrees of SPAAC crosslinks and physical crosslinks formed by mixing non-degradable or degradable azide- and DBCO-terminated 4-armPEG macromer building blocks in various ratios.

The present invention solves the problem by quantitatively altering the degrees of covalent SPAAC crosslinks vs. non-covalent crosslinks, for example, driven by hydrophobic and H-bonding interactions between untethered DBCO end groups (FIG. 1, bottom). Furthermore, the precisely tunable matrix stiffness, plasticity and degradative property of ClickGels are demonstrated to translate into an improved 3D synthetic hydrogel allowing for long-term encapsulation and timed release properties. This is of profound significance because matrix assisted chondrocyte delivery is a vital clinical treatment option for articular cartilage lesion, which is known for limited self-repair and regenerative capability due to its avascular, aneural nature and a dense ECM that impedes autologous cell migration.

Cartilage is an anisotropic tissue with complex dynamic mechanical properties that change throughout development. The local stiffness of the ECM surrounding the chondrocytes is much lower than that of the bulk adult cartilage tissue. (Alexopoulos, et al. 2005 *J. Biomech.* 38 (3), 509; Guilak, et al. 1999 *Osteoarthritis Cartilage* 7 (1), 59.) Previous work suggests that low stiffness hydrogel scaffolds could help promote chondrocyte proliferation and maintain chondrogenic phenotype. (Wang, et al. 2017 *Biomaterials* 120, 11; Callahan, et al. 2013 *Acta Biomater.* 9 (4), 6095.) However, minimal stiffness requirement of 3D hydrogel matrices and the benefit of controlled introduction of matrix plasticity/viscoelasticity for ensuring viability, proliferation, chondrogenic ECM deposition of encapsulated chondrocytes has not been established. The ability to weaken or strengthen ClickGel via precise tuning of the degrees of covalent SPAAC and DBCO-DBCO physical crosslinking, which may be dynamically disrupted and reformed to accommodate cellular mass expansion, by mismatching the ratio of DBCO- vs. N$_3$-terminated macromers at a given overall polymer content offers an exciting opportunity to interrogate the impact of biomechanical cues on the cellular behavior of encapsulated chondrocytes.

In one aspect, the invention generally relates to a hydrogel comprising a 3-dimentional crosslinking network of a combination of covalent crosslinking (CX) and non-covalent crosslinking (NCX) of hydrophilic branched polymers,

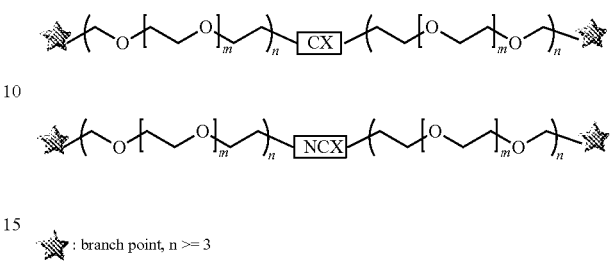

wherein the hydrophilic branched polymers are star-branched with at least 3 arms.

In certain embodiments, the physical interactions are selected from the group consisting of hydrophobic-hydrophobic interaction, π-π stacking, hydrogen bonding, electrostatic interaction, polar interaction, or a combination of one or more thereof.

In certain embodiments, the hydrophilic branched polymers are linked to NCX or CX via one or more labile linkages and/or one or more stable linkages.

In certain embodiments, the one or more labile linkages are susceptible to hydrolysis.

Exemplary labile linkages that are susceptible to hydrolysis include esters, carbonates, orthoester, anhydride, and thioester.

In certain embodiments, the one or more labile linkages include a peptide moiety cleavable by one or more enzymes (e.g., matrix metalloproteinase (MMP)).

In certain embodiments, the hydrophilic branched polymers are linked to NCX or CX via one or more stable linkages that are resistant to hydrolysis or enzyme cleavage. Exemplary stable linkages include amide, C—C(carbon-carbon single bond), C=C (carbon-carbon double bond), C≡C (carbon-carbon triple bond), ether (C—O—C), urethane (carbamate) linkages.

In certain embodiments, the hydrophilic polymers are branched polyethylene glycol (PEG), for example, with 3, 4, 5 or more arms or branches.

Any suitable covalent crosslinking (CX) may be utilized. In certain embodiments, the covalent crosslinking (CX) is formed by copper-free, strain-promoted azide-alkyne cycloaddition or copper-catalyzed azide-alkyne cycloaddition. In certain embodiments, the covalent crosslinking (CX) is formed by a click chemistry coupling between:

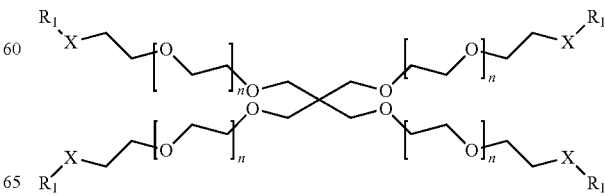

wherein $R_1$ is a group comprising —$N_3$, X is selected from ester and carbonate groups or is absent, and each n is independently an integer from about 1 to about 400 (e.g., from about 10 to about 400, from about 100 to about 400, from about 200 to about 400, from about 1 to about 200, from about 1 to about 100, from about 1 to about 50, about 50 to about 100, from about 1 to about 10, from about 3 to about 100, from about 3 to about 50, from about 3 to about 20, from about 3 to about 10); and

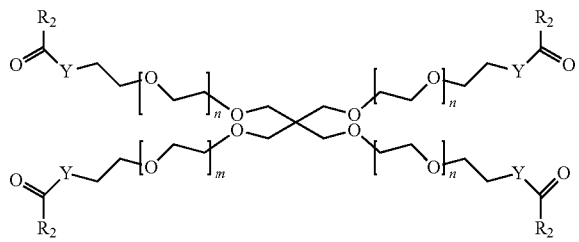

wherein $R_2$ is

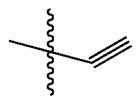

or a group comprising a cyclic or acylic alkyne group, Y is selected from —NH— and —O— groups or absent, and each m is independently an integer from about 1 to about 400 (e.g., from about 10 to about 400, from about 100 to about 400, from about 200 to about 400, from about 1 to about 200, from about 1 to about 100, from about 1 to about 50, about 50 to about 100, from about 1 to about 10, from about 3 to about 100, from about 3 to about 50, from about 3 to about 20, from about 3 to about 10).

In certain embodiments, $R_2$ is

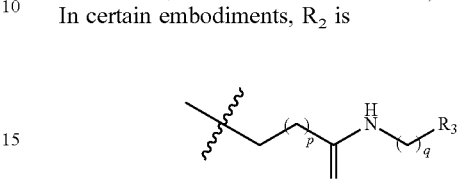

wherein $R_3$ is a group comprising a group comprising a cyclic or acyclic alkyne group, each of p and q is an integer from about 1 to about 6 (e.g., 1, 2, 3, 4, 5, 6).

In certain embodiments, $R_3$ comprises a group selected from dibenzylcyclooctyne (DBCO), dibenzocyclooctyne-amine, dibenzocyclooctyne-N-hydroxysuccinimidyl ester, (1R,8S,9s)-Bicyclo[6.1.0]non-4-yn-9-ylmethanol, (1R,8S, 9s)-bicyclo[6.1.0]non-4-yn-9-ylmethyl N-succinimidyl carbonate, and dibenzocyclooctyne-maleimide groups.

In certain embodiments, the covalent crosslinking (CX) is formed by a click chemistry coupling of:

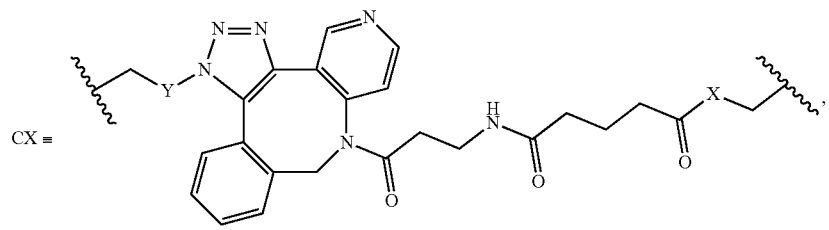

Covalent crosslink formed by SPAAC reaction
(non-degradable and degradable)

and the non-covalent crosslinking (NCX) of hydrophobic and hydrogen-bonding interactions between un-coupled DBCO moieties:

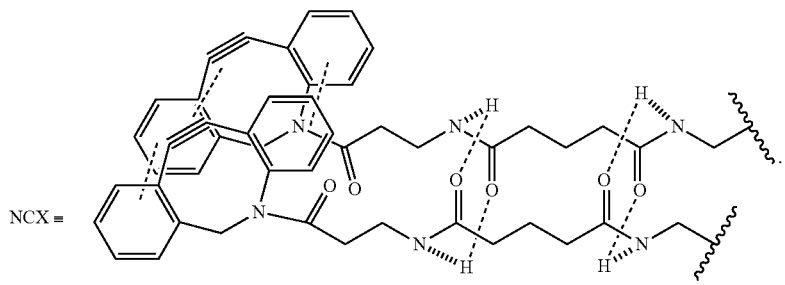

Non-covalent crosslink driven by hydrophobic & H-bonding
interactions between untethered DBCO end groups The degree of covalent crosslinking (CX) vs non-covalent crosslinking (NCX) may be adjusted as needed. In certain embodiments, about 100% to 10% (e.g., about 100% to 20%, about 100% to 30%, about 100% to 40%, about 100% to 50%, about 90% to 10%, about 80% to 20%, about 70% to 20%, about 70% to 30%, about 70% to 40%) are covalent SPAAC crosslinks and 0% to 90% (e.g., about 0% to about 80%, about 0% to about 70%, about 0% to about 60%, about 0% to about 50%, about 10% to about 90%, about 20% to about 80%, about 30% to about 80%, about 30% to about 70%, about 30% to about 60%) are DBCO-DBCO non-covalent crosslinks.

The polymer content may also be adjusted as needed. In certain embodiments, the polymer content is from about 1% to about 20% (e.g., from about 1% to about 15%, from about 1% to about 10%, from about 1% to about 8%, from about 1% to about 5%, 2.5% to about 10%, from about 2.5% to about 8%, from about 2.5% to about 7%, from about 2.5% to about 6%, from about 2.5% to about 5%, from about 5% to about 10%, from about 10% to about 15%, from about 15% to about 20%).

The hydrogel of the invention may be prepared to exhibit pre-selected properties such as stiffness, plasticity/viscoelasticity and degradation characteristics. For example, the hydrogel may be characterized by one or more of followings: a compressive stiffness from about 0.2 KPa to about 20 KPa (e.g., from about 0.2 KPa to about 15 KPa, from about 0.2 KPa to about 12 KPa, from about 0.2 KPa to about 10 KPa, from about 1 KPa to about 20 KPa, from about 1 KPa to about 15 KPa, from about 1 KPa to about 10 KPa, from about 3 KPa to about 20 KPa, from about 5 KPa to about 20 KPa); a swelling ratio from about 1.5 to about 150 (e.g., from about 15 to about 120, from about 15 to about 100, from about 15 to about 70, from about 15 to about 50, from about 25 to about 150, from about 50 to about 150, from about 70 to about 150); or a disintegration rate from about <2 days to about >1 year (e.g., from about 2 days to about 250 days, from about 2 days to about 150 days, from about 2 days to about 60 days, from about 2 days to about 30 days, from about 3 days to about 14 days, from about 7 days to about 1 year, from about 14 days to about 1 year). The hydrogel of the invention may be prepared to exhibit viscoelasticity as characterized with any degrees of creep/stress-relaxation behavior.

In another aspect, the invention generally relates to a hydrogel composition comprising a hydrogel disclosed herein and a biologically active payload encapsulated therein.

In certain embodiments, a partial or complete de-crosslinking of the hydrogel partially or completely releases the biologically active payload.

Any suitable biologically active payload may be encapsulated.

In certain embodiments, the biologically active payload comprises cells. In certain embodiments, the cells are mammalian cells or cell aggregates (e.g., cell pellets and/or organoids) selected from embryonic stem cells, induced pluripotent stem cells, mesenchymal stem cells, bone marrow stromal cells, hematopoietic stem cells, osteoblasts, chondrocytes, endothelial cells, epithelial cells, myoblasts, periosteal cells, beta cells, neutral cells, any cells differentiated from various embryonic and adult stem cells, or cell lines.

In certain embodiments, the biologically active payload comprises a biomolecule selected from the group consisting of proteins, growth factors, cytokines, and chemokines. In certain embodiments, the biologically active payload comprises the biologically active payload comprises a bone morphogenetic protein-2, 4, 6, 7 or 2/7 heterodimer (BMP-2, BMP-4, BMP-6, BMP-7, BMP-2/7).

In certain embodiments, the biologically active payload comprises the biologically active payload comprises a transforming growth factor (TGF) beta, stromal cell-derived factor 1 (SDF1), Indian hedgehog homolog (Ihh), fibroblast growth factor (FGF), insulin-like growth factor (IGF), or vascular endothelial growth factor (VEGF), or various neural induction factors.

In certain embodiments, the biologically active payload comprises a biomolecule selected from the group consisting of a nucleic acid, gene vector, bioactive lipid factor, such as sphingosine-1-phosphate (SIP), and bacterial phage.

In certain embodiments, the biologically active payload comprises a mineral (e.g., calcium apatites, calcium phosphates, hydroxyapatite, and substituted hydroxyapatites).

The hydrogel composition of invention are designed to be suitable for use in situ delivery of a variety of agents, for example, therapeutic or diagnostic agents, tissue repair and regeneration implants.

The hydrogel composition of the invention may be prepared to exhibit pre-selected properties such as stiffness, plasticity and degradation characteristics. For example, the hydrogel composition may be characterized by one or more of followings: a compressive stiffness from about 0.2 KPa to about 20 KPa (e.g., from about 0.2 KPa to about 15 KPa, from about 0.2 KPa to about 12 KPa, from about 0.2 KPa to about 10 KPa, from about 1 KPa to about 20 KPa, from about 1 KPa to about 15 KPa, from about 1 KPa to about 10 KPa, from about 3 KPa to about 20 KPa, from about 5 KPa to about 20 KPa); a swelling ratio from about 15 to about 150 (e.g., from about 15 to about 120, from about 15 to about 100, from about 15 to about 70, from about 15 to about 50, from about 25 to about 150, from about 50 to about 150, from about 70 to about 150); or a disintegration rate from about 2 days to about 1 year (e.g., from about 2 days to about 250 days, from about 2 days to about 150 days, from about 2 days to about 60 days, from about 2 days to about 30 days, from about 3 days to about 14 days, from about 7 days to about 1 year, from about 14 days to about 1 year). The hydrogel of the invention may be prepared to exhibit a viscoelasticity as characterized with any degree of creep/stress-relaxation behavior. The hydrogel or hydrogel composition of the invention are preferably cytologically compatible.

In yet another aspect, the invention generally relates to a device or implant that includes a hydrogel or a hydrogel composition disclosed herein.

The device or implant may be any suitable medical device or implant, for either human or animal use. Exemplary devices and implants include 3D in vitro tissue models or synthetic niche for 3D cell expansion.

In yet another aspect, the invention generally relates to a method for modulating one or more properties of a hydrogel. The method includes: incorporating in the hydrogel a 3-dimentional crosslinking network of a combination of covalent crosslinking (CX) and non-covalent crosslinking (NCX) of hydrophilic branched polymers,

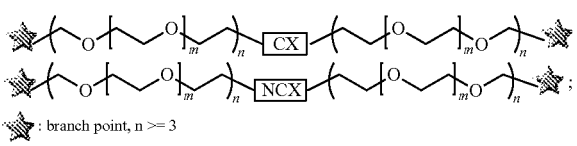

adjusting and/or controlling the ratio of covalent crosslinking (CX) to non-covalent crosslinking (NCX) of hydrophilic branched polymers; and adjusting and/or controlling the placement and ratio of one or more labile linkages to one or more stable linkages in the hydrophilic branched polymers. The hydrophilic branched polymers are star-branched with at least 3 arms. The property is one or more selected from viscoelasticity, stiffness and degradation.

In certain embodiments, the ratio of covalent crosslinking (CX) to non-covalent crosslinking (NCX) is from about 1:10 to about 10:1 (e.g., from about 1:8 to about 8:1, from about 1:5 to about 5:1, from about 1:3 to about 3:1, from about 1:2 to about 2:1, about 1:1).

In certain embodiments, the ratio of one or more labile linkages to one or more stable linkages is from about 1:0 to about 0:1 (e.g., from about 1:0.2 to about 0.2:1, from about 1:0.5 to about 0.5:1, from about 1:0.2 to about 0.2:1).

In yet another aspect, the invention generally relates to a method for delivering a biologically active payload. The method includes: placing in a subject in need thereof a device or implant comprising a hydrogel or hydrogel composition disclosed herein, and causing a controlled release of the biologically active payload.

This present invention presents a new approach for precisely tuning hydrogel stiffness and matrix plasticity via the explicit control over the degree of covalent SPAAC crosslinking vs. dynamic physical crosslinks between untethered end groups of biorthogonal macromer building blocks. Conventional methods of modulating synthetic hydrogel stiffness by increasing polymer fractions or covalent crosslinking degrees could be detrimental to the proliferation and long-term viability of encapsulated cells. Modulation of viscoelasticity of natural polymers such as alginate-based hydrogels involve the use of alginate of different molecular weights, adjustment of degrees of $Ca^{2+}$-crosslinking, and the covalent attachment of other polymer tethers. In contrast, with only 2 pairs of designer building blocks (4-armPEG end-functionalized with DBCO or azide via stable or labile linkers), the present invention offers ClickGels with a broad range of stiffness, plasticity and degradative properties could be prepared by simply altering their mixing ratio along with cells of interest.

By introducing robust yet dynamic physical crosslinks between untethered DBCO end groups at the expense of reduction in SPAAC crosslinks, enhancement in both ClickGel stiffness and network plasticity can be achieved, permitting more robust proliferation and matrix deposition of encapsulated chondrocytes.

The invention additionally allows controlled degradation in ClickGels to achieve predictable disintegration over a broad range by strategic placement of a single labile linkage on either side of the SPAAC crosslink, and that ClickGel degradation promoted both proliferation and chondrogenic matrix deposition of encapsulated mouse or human chondrocytes. Finally, timed release of chondrocytes from degradable ClickGels was accomplished without negatively affecting the viability or chondrogenic phenotypes of released chondrocytes.

These properties combined make ClickGels, a wholly synthetic platform free of biological contaminants and with readily and reproducibly tunable physical and mechanical properties, uniquely suited as 3D synthetic niches for chondrocyte encapsulation, in vitro expansion and timed release. It could also benefit the ex vivo expansion of scarcely available stem cells (e.g., hematopoietic stem cells) known to be difficult to expand/enrich via conventional 2D cultures for other cell-based therapies. More broadly speaking, the novel concept of engineering network viscoelasticity via controlled integration of dynamic physical crosslinks and the strategic placement of single labile linkages near crosslinking sites provide exciting new tools for engineering 3D cellular niches and tissue models for regenerative medicine and drug discovery applications.

The following examples are meant to be illustrative of the practice of the invention, and not limiting in any way.

EXAMPLES

Partially or perfectly ([DBCO]:[$N_3$]=1) SPAAC-crosslinked non-degradable ClickGels (FIG. 1) with tunable compressive stiffness and swelling behavior were prepared by systemically altering the molar ratios of non-degradable 4-armPEG-azide (Y=absent) to non-degradable 4-armPEG-amide-DBCO (X=NH) mixed in PBS (5 w/v % polymer content), for example, from 1:0.6 to 0.6:1.

The partially SPAAC-crosslinked ClickGels formed with an excess of 4-armPEG-azide ([DBCO]:[$N_3$]<1) exhibited much higher swelling ratios (FIG. 2a) and significantly weaker compressive moduli (FIG. 2b) than the perfectly SPAAC-crosslinked ClickGel. The observed 2-fold increase in swelling ratio and 2-fold decrease in compressive stiffness (at the 0-30% strain range) when [DBCO]:[azide] changed from 1:1 to 0.6:1 can be attributed to the reduced percentage of SPAAC covalent crosslinks, thus a more loosely tethered 3D ClickGel network.

Figure 2:
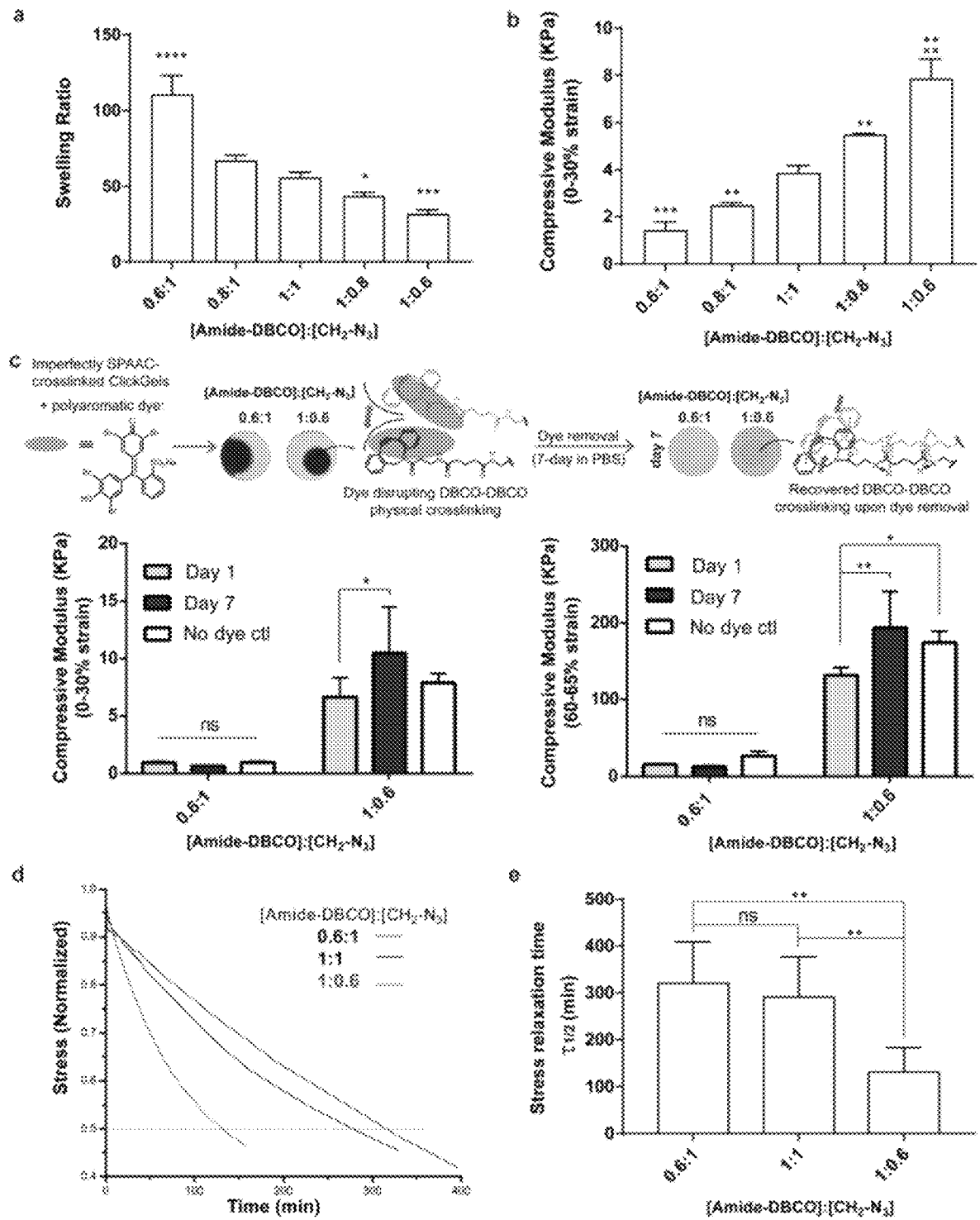
FIG. 2. Non-degradable ClickGels (5 w/v %) crosslinked between mismatched ratios of DBCO- and $N_3$-terminated macromers exhibit tunable swelling behavior, stiffness and viscoelasticity, with stiffer ClickGels formed with excess DBCO-terminated macromers exhibiting faster stress relaxation. (a) Swelling ratio. (b) Compressive moduli (0-30% strain) of ClickGels crosslinked between varying ratios of DBCO- and $N_3$-terminated macromers. (c) Compressive modulus changes (0-30% and 60-65% stain ranges) upon the addition and removal of polyaromatic dye (bromophenol blue sodium salt). (d) Representative stress relaxation profiles of ClickGels composed of varying ratios of DBCO- and $N_3$-terminated macromers. (e) Stress relaxation time ($\tau_{1/2}$) of varying ratios of DBCO- and $N_3$-terminated macromers. ns: $p>0.05$; $*p<0.05$; $p<0.01$; $*p<0.001$; $*****p<0.0001$ (a, b: one-way ANOVA with Dunnett's multiple comparisons vs. the 1:1 formulation; c & e: two-way and one-way ANOVA with Tukey's multiple comparisons, respectively). (f) Shear stress relaxation time of a ClickGel with [amide-DBCO]:[CH2-$N_3$]=1:0.6 determined as 1268.2±304.7 (mean±S.D.). ClickGel disc (8-mm in diameter, n=5) was equilibrated in PBS for 24 hours. Strain sweep and frequency sweep test were performed on an AG2000 rheometer to determine the linear viscoelastic region. Shear stress relaxation time was measured upon the application of a constant shear strain of 10% (5 s rise time).
Figure 2:
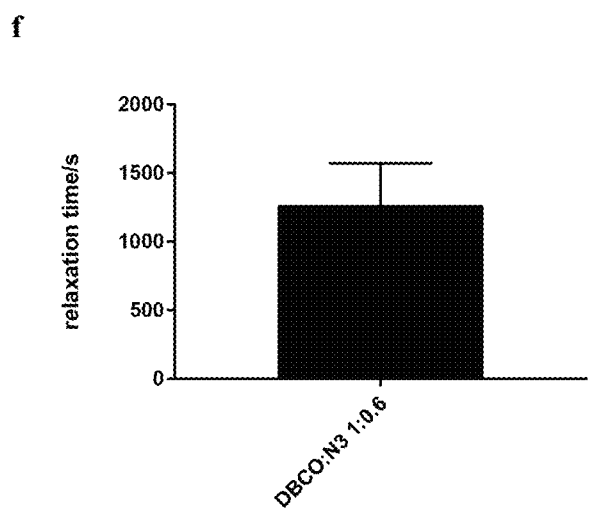

By contrast, partially SPAAC-crosslinked ClickGels formed with an excess of 4-armPEG-DBCO macromers exhibited significantly higher compressive moduli and much lower swelling ratios compared to the perfectly SPAAC-crosslinked ClickGel (FIGS. 2a & 2b). The fold decrease in swelling ratio and 2-fold increase in compressive stiffness can be attributed to the increasing physical crosslinks between untethered DBCO's when [DBCO]: [$N_3$] changed from 1:1 to 1:0.6.

These physical crosslinks, presumably driven by a combination of hydrophobic interaction between the tricycles of DBCO's and H-bonding interactions between adjacent amide linkages (FIG. 1), were robust enough to overcome the reduction in covalent SPAAC crosslinks, resulting in a mechanically strengthened 3D network. The mechanical contribution of DBCO-DBCO physical crosslinks within the imperfectly SPAAC-crosslinked system (e.g., [DBCO]:[$N_3$]=1:0.6) was validated by the reduction in compressive moduli upon addition of polyaromatic dye to disrupt the DBCO-DBCO interaction (day 1, FIG. 2c). Furthermore, the ability of untethered DBCO groups to reform physical crosslinks was evidenced by the restoration of the compressive moduli of the hydrogel upon dye removal (after 7-day equilibration in PBS) to the level of ClickGels without dye treatment (FIG. 2c), supporting the dynamic/reversible nature of the DBCO-DBCO crosslinks. By contrast, the addition and removal of the polyaromatic dye to and from the imperfectly SPAAC-crosslinked ClickGels with azides in excess (e.g. [DBCO]:[$N_3$]=0.6:1) did not cause significant perturbations in their stiffness (FIG. 2c), supporting negligible physical crosslinks between untethered azide-terminated chains. Further demonstrating the robustness of DBCO-DBCO physical crosslinks was the observation that gelling occurred at a mismatched ratio as drastic as [DBCO]:[$N_3$]=1:0.3, with the resulting ClickGel possessing only 30% covalent SPAAC crosslinks but 70% DBCO-DBCO physical crosslinks stiffer than those formed at [DBCO]:[$N_3$]=0.6:1 and 0.8:1 (FIG. 8). By contrast, formulations with a significant fraction of excess azide endgroups ([DBCO]: [$N_3$]=0.3:1, 0.4:1 or 0.5:1) could barely gel into network with sufficient integrity due to lack of physical crosslinking among excess azide groups, despite the 30-50% of covalent SPAAC crosslinks.

Viscoelastic hydrogels are attractive for cell encapsulation due to their ability to better accommodate cell spreading, migration, proliferation and matrix deposition through more effective/faster stress relaxation. Here we show that engineering the reversible DBCO-DBCO physical crosslinks into the wholly synthetic network translated into significantly faster stress relaxation in these stiffer hydrogels (FIGS. 2d & 2e). Specifically, stress relaxation ($\tau_{1/2}$) in hydrogels formed with excess DBCO-terminated macromers (e.g. [DBCO]:[$N_3$]=1:0.6, 131±52 min) was significantly faster than hydrogels with 100% SPAAC-crosslinking (DBCO): [$N_3$]=1:1, 291±85 min) or those formed with excess azide-terminated macromers ([DBCO]: [$N_3$]=0.6:1, (320±88 min). These data support that dynamic DBCO-DBCO physical crosslinks (their breakage and reformation) are more effective in dissipating energy than any potential physical interactions between the SPAAC crosslinks or the untethered azide-terminated PEG arms in the weaker ClickGels. There is likely some level of hydrophobic interactions among the triazole moieties of the SPAAC crosslinks, the disruption of which may have expedited energy dissipation to a degree comparable to that due to the mobility of untethered PEG-azide arm (no statistically significant difference in $\tau_{1/2}$, [DBCO]: [$N_3$]=1:1 vs. [DBCO]: [$N_3$]=0.6:1; FIG. 2e). It should be noted that the time scale of shear stress relaxation time $\tau_{1/2}$ determined for these hydrogels were much faster, although their general trend remain the same. For instance, the shear stress relaxation time $\tau_{1/2}$ of a ClickGel with [amide-DBCO]:[CH2-$N_3$]=1:0.6 was determined as 1268.2±304.7 seconds (FIG. 2f) as opposed to 131±52 min under compressive mode on DMA.

Further validating the robustness of DBCO-DBCO physical crosslinks was the observation that gelling occurred at mismatched ratio as drastic as [DBCO]:[$N_3$]=1:0.3, which comprised only 30% covalent SPAAC crosslinks and 70% DBCO-DBCO physical crosslinks, resulting in a ClickGel stiffer than that formed at [DBCO]:[$N_3$]=0.6:1 or 0.8:1 (FIG. 8). By contrast, formulations with [DBCO]:[$N_3$]=0.3:1, 0.4:1 or 0.5:1 could barely gel into network with sufficient integrity due to lack of physical crosslinking among excess azide groups, despite the 30-50% of covalent SPAAC crosslinks.

To determine a suitable cell encapsulation density within ClickGels, we monitored the viability of iMACs encapsulated at an initial density ranging from 100000 to 1000000 cells per 25-µL perfectly SPAAC-cross-linked nondegradable ClickGel (5 w/v %) and cultured in expansion media over 8 weeks (FIG. 9a). Whereas iMACs were able to proliferate within the ClickGel during the first 3-4 weeks at all encapsulation densities examined, the number of viable cells in those with very high initial encapsulation densities (750000 and 1000000 iMACs per gel) quickly declined after 6 weeks, with dead cells localized deeper within the gel due to possible nutrient deprivation. The initial encapsulation density of 250000 iMACs per gel resulted in the most viable cells by 8 weeks (FIG. 9b) while maintaining the expression of chondrogenic markers type II collagen and aggrecan (FIG. 9c). This encapsulation density was thus utilized to investigate the impact of ClickGel stiffness on resident cells.

Stiffer ClickGels with dynamic DBCO-DBCO physical crosslinks ([DBCO]:[$N_3$]>1) supported better cell proliferation of the encapsulated iMACs over 4 weeks in EM compared to those encapsulated in the perfectly SPAAC-crosslinked ClickGel (FIG. 2a), along with more robust type II collagen expression by iMACs in the stiffer gels (FIG. 2c).

Figure 3:
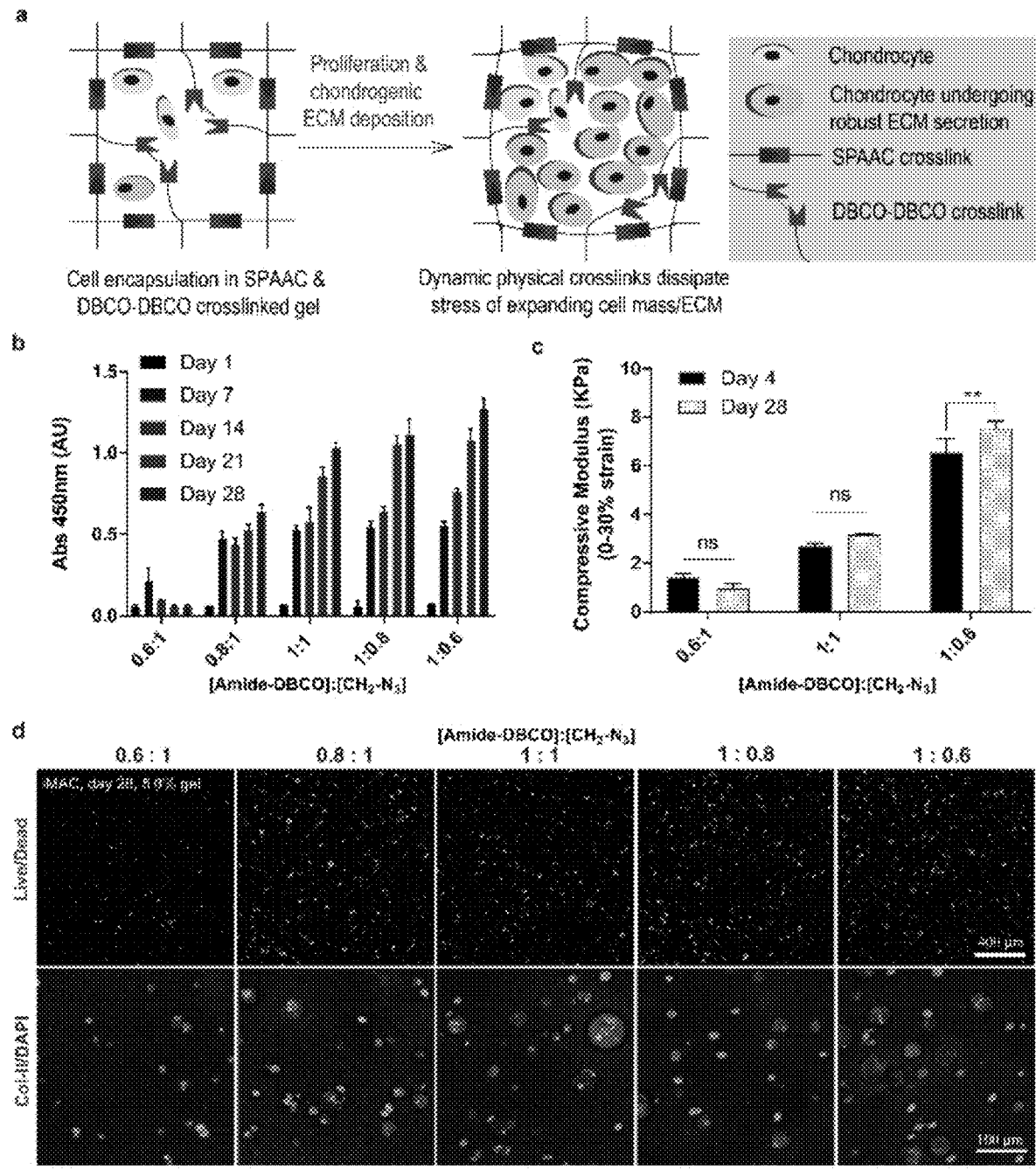
FIG. 3. Stiffer non-degradable ClickGels (5 w/v %) with dynamic DBCO-DBCO physical crosslinks better accommodate the proliferation and chondrogenic ECM deposition of encapsulated iMACs over time. (a) Depiction of reversible formation of DBCO-DBCO crosslinks helping dissipate stress imposed by the expanding cell mass ECM deposition by encapsulated cells. (b) Viability of encapsulated iMACs over time. (c) Temporal changes in compressive moduli (0-30% strain) of iMAC-laden ClickGels over 28-day culture. (d) Live (green)/dead (red) staining and type II collagen (green)/DAPI (blue) immunofluorescent staining of iMAC-laden ClickGels after 28-day culture. 250,000 iMACs were encapsulated in 25-μL 5 wt % non-degradable ClickGels of varying macromer ratios and cultured in expansion media. ns: $p>0.05$; $**p<0.01$ (two-way ANOVA with Sidak's multiple comparisons).

Using the optimized initial cell encapsulation density (25,000 cells/25-µL gel) and polymer content of ClickGel (5 w/v %), we tested the hypothesis that stiffer ClickGels with dynamic DBCO-DBCO physical crosslinks ([DBCO]:[$N_3$]>1) constitute a more adaptive/permissive niche environment for cell proliferation and ECM deposition (FIG. 3a). Indeed, the stiffer and more viscoelastic ClickGel strengthened by DBCO-DBCO crosslinks supported better cell proliferation of the encapsulated iMACs over 4 weeks in EM compared to those encapsulated in the perfectly SPAAC-crosslinked ClickGel (FIG. 3b), accompanied with more robust type II collagen expression (FIG. 3d). By contrast, in the absence of DBCO-DBCO physical crosslinks, iMACs encapsulated within the weaker and less viscoelastic ClickGels ([DBCO]:[$N_3$]<1) exhibited poorer cell proliferation and viability beyond the first week, with the ClickGel with the most untethered azide-terminated PEG arms ([DBCO]: [$N_3$]=0.6:1) being the least favorable 3D environment for iMACs. Consistent with these observations, only the stiffer and more viscoelastic iMAC-laden ClickGel ([DBCO]: [$N_3$]=1:0.6) exhibited statistically significant enhancement in stiffness, presumably due to more robust ECM deposition, after 4-week culture in EM (FIG. 3c).

Figure 4:
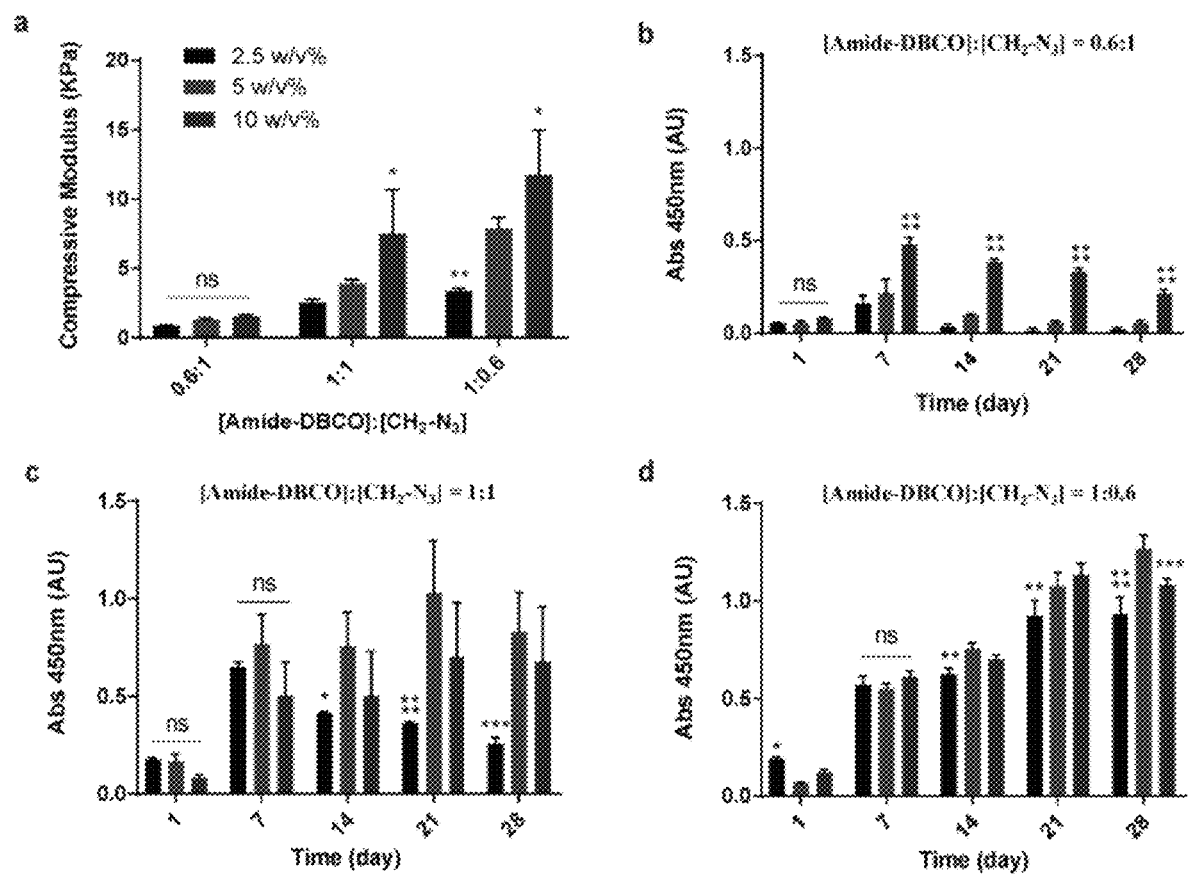
FIG. 4. Polymer contents further modulate stiffness of non-degradable ClickGels crosslinked between varying ratios of DBCO- and N3-terminated macromers and the cellular proliferation of encapsulated iMACs over time. a. Compressive moduli (0-30% strain) as a function of Click-Gel polymer content and ratios of DBCO- and N3-terminated macromers. b-d. Viability of encapsulated iMACs over time as a function of ClickGel polymer content in ClickGels crosslinked from different ratios (b. 0.6:1; c. 1:1; d. 1:0.6) of DBCO- and $N_3$-terminated macromers. 250,000 iMACs were encapsulated in 25-μL 2.5, 5 or 10 wt % non-degradable ClickGels of varying macromer ratios and cultured in expansion media. ns: $p>0.05$; $*p<0.05$; $p<0.01$; $*p<0.001$; $*****p<0.0001$ (two-way ANOVA with Tukey's multiple comparisons vs. the 5 w/v % gel).

As polymer content is also known to affect the mechanical properties of crosslinked hydrogels, we investigated whether and how modulating ClickGel polymer content along with the degree of SPAAC/physical cross-links synergistically affect their compressive moduli and the cellular behavior of encapsulated iMACs. As expected, increasing and decreasing polymer content by 2-fold (from 5 to 10 or 2.5% w/v) in perfectly SPAAC-cross-linked or stiffer ClickGels with excess DBCO's resulted in proportional enhancement and reduction in compressive moduli, respectively (FIG. 4a). In the much weaker ClickGel formulation where azide residues were in large excess ([DBCO]:[$N_3$]=0.6:1), increasing or decreasing the polymer content failed to yield statistically significant changes in compressive moduli (<2-kPa compressive modulus). However, the benefit of increasing polymer contents in these weak ClickGels from 5 to 10% w/v was manifested by statistically significant increase in early proliferation of encapsulated iMACs within the first week and their subsequent viability over 4 weeks (by 1-4 fold increase; FIG. 4b). In the perfectly SPAAC-cross-linked ClickGels, reducing polymer content from 5 to 2.5% w/v (compressive moduli from 3.9 to 2.5 kPa) negatively impacted both the proliferation and long-term viability of encapsulated iMACs (FIG. 4c). Whereas iMACs encapsulated in 5% w/v perfectly SPAAC-cross-linked ClickGel were able to proliferate at least for 3 weeks, those encapsulated in 2.5% w/v ClickGel only proliferated within the first week and saw significant decline in viable cells starting week 2, further supporting that a minimal stiffness threshold for sustained proliferation (3-4 weeks) is likely over 2.5 kPa. Interestingly, there was no statistically significant benefit for the proliferation/viability of encapsulated iMACs by increasing polymer content from 5 to 10% w/v (compressive moduli from 3.9 to 7.5 kPa) in the perfectly SPAAC-crosslinked ClickGel (FIG. 4d). This observation suggests that once the stiffness of a synthetic niche falls within a suitable range, further increasing the stiffness at the cost of increasing polymer content (which may negatively impact nutrient/waste transport in and out of the 3D network) may not be beneficial. For the much stiffer yet more viscoelastic Click-Gel with substantial DBCO-DBCO physical cross-links ([DBCO]:[$N_3$]=1:0.6), reducing polymer content from 5 to 2.5% w/v (compressive modulus from 7.9 to 3.3 kPa) slowed the proliferation after 2 weeks and resulted in reduced overall viable cells by 4 weeks. Meanwhile, increasing its polymer content from 5 to 10% w/v (compressive modulus from 7.9 to 11.8 KPa) did not benefit proliferation/viability of encapsulated iMACs. The overall cell viability within the 10% w/v stiffest gel in fact reduced by 4 weeks, again supporting that increasing the stiffness beyond a certain range at the cost of increasing polymer content may not be beneficial. It is worth noting that despite the similar compressive moduli of 10% w/v perfectly SPAAC-crosslinked (7.5 kPa) vs. 5% w/v DBCO-DBCO strengthened (7.9 kPa) ClickGels, the latter better supported sustained proliferation and viability of encapsulated iMACs over 4 weeks.

Increasing and decreasing polymer content of ClickGels resulted in proportional enhancement and reduction in their compressive moduli (FIG. 4a), but the benefit of increasing polymer contents on early cell proliferation (first week) was only manifested in the much weaker imperfectly SPAAC-crosslinked ClickGels with excess untethered azide chains ([DBCO]:[$N_3$]=0.6:1) (FIG. 4b). In both perfectly SPAAC-crosslinked ClickGels and the stiffer and more viscoelastic ClickGels with DBCO-DBCO crosslinking, reducing polymer content from 5 to 2.5 w/v % (compressive moduli from 3.9 kPa to 2.5 kPa and from 7.9 kPa to 3.3 kPa, respectively) negatively impacted both the proliferation and long-term viability of encapsulated iMACs (FIGS. 4c & 4d). There was no significant benefit for increasing polymer content from 5 to 10 w/v % in these ClickGels. This observation suggests that once the stiffness of a synthetic niche falls within a suitable range, further increasing the stiffness at the cost of increasing polymer content (which could negatively impact nutrient/waste transport in and out of the 3D network) may not be beneficial. It is worth noting that despite the similar compressive moduli of 10 w/v % perfectly SPAAC-crosslinked (7.5 kPa) vs. 5 w/v % partially SPAAC-crosslinked and DBCO-DBCO strengthened more viscoelastic (7.9 kPa) ClickGels, the latter better supported sustained proliferation and viability of encapsulated iMACs over 4 weeks. Overall, these experiments reveal ~3 kPa as a likely lower threshold for the ClickGel system below which the encapsulated iMACs could not undergo sustained proliferation. Beyond this threshold, introducing dynamic DBCO-DBCO physical crosslinks is advantageous to polymer content increases as a means to improve the stiffness of the chondrogenic cellular niche.

Interestingly, there was no statistically significant benefit for the proliferation/viability of encapsulated iMACs by increasing polymer content from 5 to 10 w/v % (compressive moduli from 3.9 kPa to 7.5 kPa) in the perfectly SPAAC-crosslinked ClickGel. This observation suggests that once the stiffness of a synthetic niche falls within a suitable range, further increasing the stiffness at the cost of increasing polymer content (which may negatively impact nutrient/waste transport in and out of the 3D network) may not be beneficial.

For the much stiffer partially SPAAC-crosslinked Click-Gel with substantial DBCO-DBCO physical crosslinks ([DBCO]:[$N_3$]=1:0.6), reducing polymer content from 5 to 2.5 wt % (compressive modulus from 7.9 kPa to 3.3 kPa) slowed the proliferation after 2 weeks and resulted in reduced overall viable cells by 4 weeks. Meanwhile, increasing its polymer content from 5 to 10 w/v % (compressive modulus from 7.9 kPa to 11.8 KPa) did not benefit proliferation/viability of encapsulated iMACs. The overall cell viability within the 10 w/v % stiffest gel in fact reduced by 4 weeks, again supporting that increasing the stiffness beyond a certain range at the cost of increasing polymer content may not be beneficial.

It was observed that despite the similar compressive moduli of 10 w/v % perfectly SPAAC-crosslinked (7.5 kPa) vs. 5 w/v % partially SPAAC-crosslinked and DBCO-DBCO strengthened (7.9 kPa) ClickGels, the latter better supported sustained proliferation and viability of encapsulated iMACs over 4 weeks. It is likely that the reversible nature of the physical crosslinks between untethered DBCOs translated into a more dynamic/adaptable local environment to accommodate the expanding space and help dissipate the local energy/strain imposed by the proliferating cell mass.

Overall, these experiments reveal that 3.3 kPa as a likely lower threshold compressive modulus for the ClickGel system below which the encapsulated iMACs would be unable to undergo sustained proliferation beyond 2 weeks. ClickGels with compressive moduli of 3.9-11.8 kPa are able to support sustained proliferation and cell viability over 3-4 weeks. Within this range, introducing dynamic DBCO-DBCO physical crosslinks is advantageous to increasing polymer content (which could negative impact nutrient/waste transport) as a means to improve the stiffness and introduce necessary matrix plasticity/viscoelasticity of the synthetic niche to enable sustained cell proliferation.

Figure 5:
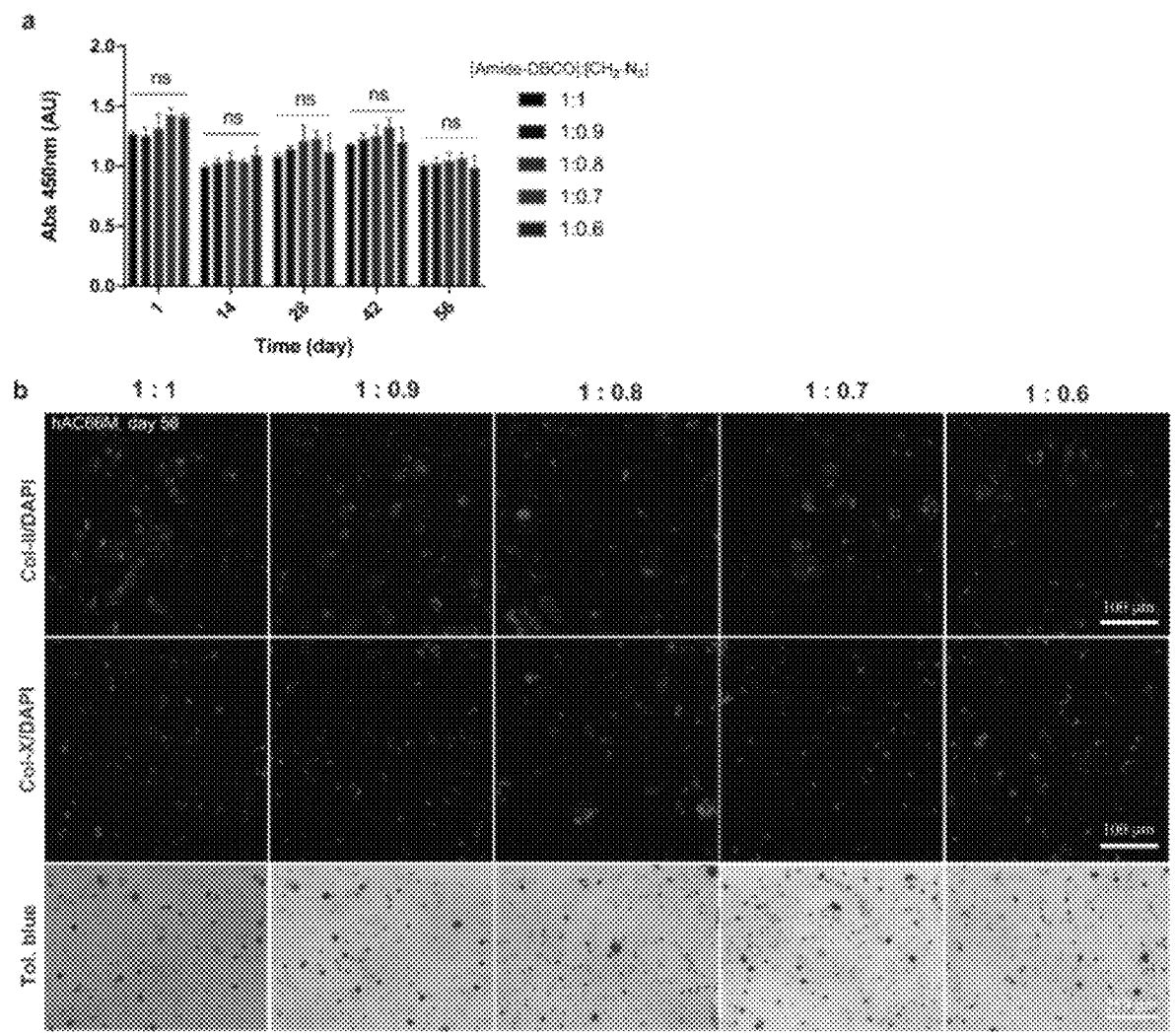
FIG. 5. Human chondrocytes encapsulated in non-degradable ClickGels maintain long-term viability and chondrocyte phenotype regardless of the ratio of DBCO- and N3-terminated macromers. a. Viability of encapsulated human chondrocytes as a function of ClickGel composition over 56 days. b. type II collagen (green)/DAPI (blue), type X collagen (green)/DAPI (blue) immunofluorescent staining and toluidine blue (for GAG) staining of human chondrocyte-laden ClickGels of varying compositions on day 56 of chondrogenic culture. 500,000 human chondrocytes were encapsulated in 25-μL 5 wt % non-degradable ClickGels of varying macromer ratios and cultured in chondrogenic media (high glucose DMEM, 40-μg/mL L-proline, 100-μg/mL sodium pyruvate, 1% insulin-transferrin-selenous acid mixture, 100-nM dexamethasone and 10-ng/mL TGF-β3).

Using the 5 w/v % perfectly SPAAC-crosslinked and the stiffer and more viscoelastic ClickGels containing various fractions of DBCO-DBCO physical crosslinks ([DBCO]:[$N_3$]=1:1, 1:0.9, 1:0.8, 1:0.7 or 1:0.6), we then validated the general applicability of the system for long-term encapsulation of human articular chondrocytes. The encapsulated hACs (500,000 cells per 25-pt gel) remained viable in all formulations examined over the 8-week culture in low-serum chondrogenic media (which promotes chondrogenic matrix synthesis rather than cell proliferation), supporting that nutrients/waste could readily penetrate in and out of these hydrophilic 3D network at this cell encapsulation density (FIG. 5a). Equally important, toluidine blue staining and immunofluorescent staining revealed robust deposition of GAG and type II collagen secretions by hACs encapsulated in all ClickGel formulations examined, with minimal type X collagen detected by week 8 (FIG. 5b; note that the hACs were isolated from the relatively healthy portion of discarded osteoarthritic joint tissues). The successful encapsulation of hACs by ClickGels and their extended in vitro culture within these 3D synthetic niches without compromised viability or chondrogenic phenotype point to promising utilities for ex vivo cartilage tissue engineering applications.

For guided cartilage tissue regeneration in vivo, it is critical to also demonstrate the feasibility of tuning the degradative properties of the ClickGel to promote the proliferation and chondrogenic matrix deposition of encapsulated cells and ensure their timely disintegration. Synchronizing the rate of synthetic niche degradation with that of the neo-tissue integration could preserve the overall mechanical integrity of the cell-laden construct throughout the dynamic guided tissue regeneration process. Too fast of a degradation will compromise the necessary stiffness necessary for maintaining active metabolism of encapsulated cells while too slow of a degradation will impede ECM (GAG and collagen fibrils are macromolecules of micron dimension) integration and eventual replacement of the synthetic niche by regenerated neotissue. (Nicodemus, et al. 2008 *Tissue engineering. Part B, Reviews* 14 (2), 149; Chu, et al. 2017 *Tissue Eng Part A* 23 (15-16), 795.)

By mixing labile 4-armPEG-ester-azide and stable 4-armPEG-azide macromers in varying ratios with the stable 4-armPEG-amide-DBCO while keeping [DBCO]:[total $N_3$]=0.7:1, 1:1 or 1:0.7, 5 w/v % ClickGels with varying degrees of SPAAC and DBCO-DBCO physical crosslinking were prepared. These ClickGels disintegrated in 18-53 days or remained intact >150 days upon incubation in EM (FIG. 6a). The weaker partially SPAAC-crosslinked ClickGels (azide in excess) with the highest labile 4-armPEG-ester-azide fraction (100%) disintegrated the fastest while the much stiffer ClickGels with DBCO-DBCO physical crosslinks containing the least fraction of labile 4-armPEG-ester-azide (60%) disintegrated the slowest. The hydrophobicity around the DBCO-DBCO physical crosslinks combined with the more densely packed network has likely slowed free water penetration to the labile ester linkage near the SPAAC crosslinks. At a given degree of SPAAC/physical crosslinking, the disintegration rate expectedly accelerated with the increasing fractions of labile 4-armPEG-ester-azide macromer. In contrast to tuning the molecular weight of degradable polymer chains, covalent crosslinking contents, or overall polymer fractions as the means of altering degradable hydrogel degradation rates, the prospectively tuning of ClickGel degradation rate by facile adjustment of the ratio of a pair of building blocks containing a single labile linkage (without altering overall polymer content) avoids excessive immunogenic acidic degradation products or poor nutrient transport associated with high polymer fractions.

Next examined was the proliferation/viability of iMACs encapsulated in perfectly SPAAC-crosslinked 5 w/v % ClickGels with various fractions of labile 4-armPEG-ester-azide over 4-week culture in EM. The iMACs encapsulated in faster-degrading ClickGels better proliferated and maintained their viability throughout 4 weeks (FIG. 6b), consistent with the higher fraction of live cells in faster degrading ClickGels at a given degree of SPAAC-crosslinking as revealed by live/dead staining (FIG. 10). The faster-degrading ClickGels also supported more robust type II collagen secretion by the encapsulated iMACs (FIG. 6c). It is worth noting that the cell-laden construct with 100% labile 4-armPEG-ester-azide did not fully disintegrate on day 28 (although some viable cells already release from the weakening gel). The slightly slower disintegration compared to the cell-free construct (which disintegrated in 25 days in EM) is likely due to the high cell mass impeding free water penetration to some extent.

When the perfectly SPAAC-crosslinked 5 w/v % ClickGel with increasing fractions of labile 4-armPEG-ester-azide were used to encapsulate hACs, more robust GAG and type II collagen secretions by encapsulated hACs were observed in all degradable formulations after 4 weeks in chondrogenic culture (FIG. 5d). The expression of hypertrophy marker type X collagen by hACs was not observed in the faster degrading formulations (75% and 100% 4-armPEG-ester-azide). These observations support that degrading synthetic niches are more conducive to chondrogenic matrix deposition by encapsulated chondrocytes in general.

Also examined was the tunable release of chondrocytes from degradable ClickGels and whether the released cells maintain their chondrogenic phenotype, which are critical for matrix assisted autologous chondrocyte implantation applications. Chondrocytes tend to lose their chondrogenic phenotype in monolayer cultures with increasing passages. Thus, chondrocyte proliferation within a degradable ClickGel niche and subsequent release without compromising their chondrogenic phenotype (FIG. 7a) could provide a promising solution.

Crystal violet staining was used to monitor the iMACs released (and adhered to the culture plate) from perfectly SPAAC-crosslinked ClickGels with varying fractions of labile 4-armPEG-ester-azide over 30 day-culture in EM (FIG. 7b). On day 10, only the ClickGel formed with 100% labile 4-armPEG-ester-azide released a small number of iMACs. On day 15, this faster-degrading ClickGel released a bulk content of encapsulated cells while the ones containing 75%, 50% or 25% labile 4-armPEG-ester-azide began to release. On day 30, the fastest-degrading ClickGel released the remaining iMACs whereas the one containing 75% labile ester-N3 linkages started to release the bulk content of its encapsulated cells. These observations support a positive correlation between the content of labile ester linkages within the ClickGel (gel disintegration rate) and cell release rate.

When varying ratios of labile 4-armPEG-ester-DBCO (100%, 50%, 0%) and stable 4-armPEG-amide-DBCO were mixed with 100% labile 4-armPEG-ester-$N_3$ to encapsulate iMACs, the same correlation was observed between labile ester linkage fractions and cell release rate, although the cell-laden constructs fully disintegrated more rapidly, on days 25, 42, and 56, respectively.

The iMACs released from these ClickGels were then pelleted and cultured in EM for another 10 days before being stained for phenotypical chondrogenic markers. Robust expression of type II collagen and GAG was observed with these iMAC pellets (FIG. 7c), supporting that these cells maintained their chondrogenic phenotype throughout their encapsulation within the degradable ClickGels as well as after their release.

Experimental

Macromer Synthesis 4-armPEG-amide-DBCO, 4-armPEG-ester-DBCO, 4-armPEG-azide and 4-armPEG-ester-azide were synthesized from 4-armPEG20k, purified and characterized by $^1$H and $^{13}$C NMR and GPC following published protocols. (Xu, et al. 2014 *J. Am. Chem. Soc.* 136 (11), 4105.)

ClickGel Preparation

All hydrogels were prepared by mixing azide-terminated and DBCO-terminated macromers in varying stoichiometric ratios in phosphate buffered saline (PBS, pH 7.4). The resultant solution was transferred into either a Teflon mold (10 mm diameter, 200 µL) for mechanical tests, onto a sterilized Parafilm for degradation test (25 µL) or swelling ratio test (50 µL). The formulation was allowed to gel at room temperature up to 15 min (weaker formulations allowed to gel longer). For ClickGels consisting of 3 macromers, the labile and stable azide-terminated macromers or DBCO-terminated macromers were first mixed separately.

Cell Encapsulation in ClickGels

A 25-4 suspension of cells, azide-terminated and DBCO-terminated macromers in varying stoichiometric ratios in PBS was mixed and pipetted onto sterilized Parafilm, and allowed to gel 2-30 min (weaker formulation allowed to gel longer) before being transferred into low-attachment 24-well plates.

Equilibrated Swelling Ratio

As-prepared 5% w/v ClickGels (50 µL) were placed into 2 mL of 0.1-M PBS (pH 7.4) each and equilibrated on an orbital shaker for 1 week at room temperature. The fully equilibrated ClickGels were dabbed by KimWipe to remove excess aqueous buffer and weighed ($W_h$). The equilibrated weight swelling ratio was determined by the weight of the fully hydrated hydrogel ($W_h$) versus the weight of the dried specimen upon lyophilization ($W_d$) using the following equation:

$$\text{weight swelling ratio} = (W_h - W_d)/W_d \quad \text{Equilibrated}$$

Compressive Moduli

Unconfined compressive test was performed on a dynamic mechanical analyzer (DMA800, TA Instruments) at 20° C. Cylindrical specimens (N=3) were compressed under the force controlled mode, ramping from 0.02 N to 12 N at 5 N/min in PBS (pH 7.4) or DMEM (for cell-laden hydrogel) in a submersion compression fixture. The slopes of the stress-versus-strain curves in the linear range of 0-30% or the higher 60-65% strain range were used for calculating the compressive moduli.

Stress Relaxation Time

The rates of stress relaxation, time taken to relax the stress to half of initial loading ($\tau_{1/2}$), of ClickGels were measured from compression tests of cylindrical specimens (N=7, pre-equilibrated in PBS for 36 h) on a dynamic mechanical analyzer (DMA800, TA Instruments) equipped with a submersion compression fixture under stress relaxation mode. All specimens were applied with a 15% constant compressive strain (ramped within 0.1 min and held throughout the test) while the load was recorded over time.

Modulating Physical Cross-Links within ClickGels with Polyaromatic Dye

As-prepared 5% w/v ClickGels (200 µL, N=3) were placed into 2 mL of 0.125-mg/mL Bromophenol Blue sodium salt solution (in PBS, pH 7.4, 1 M) and equilibrated on an orbital shaker at room temperature. After 24 h, the dye solution was removed and the ClickGels were imaged and subjected to mechanical testing as described above. The ClickGels were then equilibrated in 2-mL PBS, with daily replacement of fresh PBS for 7 days before they were imaged and subjected to mechanical testing.

Immature Murine Articular Chondrocyte (iMAC) Isolation iMAC was harvested from wild-type C57BL/6 neonates (4-6 days old) as previously described. (Huang, et al. 2016 *PLoS One* 11 (1), e0148088.) Briefly, the cartilage from knee and ankle joints were collected and digested for ~1 h in type II collagenase (Worthington) solution (3 mg/mL or 900 U/mL in high glucose DMEM). The cartilage pieces were then rinsed in PBS and transferred to a more dilute type II collagenase solution (1 mg/mL or 300 U/mL) and incubated at 37° C. on a tube rotator for 5-6 h. The digested cartilage solution was then filtered through a 70-µm nylon mesh to obtain single cell suspension. The cells were pelleted and immediately used for hydrogel encapsulation.

Human Chondrocyte (hAC) Isolation

Discarded tissues from osteoarthritic patient (age 66, male) undergoing total knee arthroplasty were collected and stored in ice cold PBS supplemented with penicillin/streptomycin for less than an hour before processing. Using a sterilized razor blade, structurally intact articular cartilage from the femoral condyles were shaved off and minced into tiny pieces. The cartilage pieces (3-5 g) were transferred to a 50-mL conical tube with type II collagenase solution (1mg/mL or 300 U/mL) and digested overnight at 37° C. on a rotator. Any residual cartilage fragments were removed by filtration through a 70-µm nylon mesh and the cell suspension was plated at a cell density of $25 \times 10^3/\text{cm}^2$. Upon reaching 80% confluency, cells were trypsinized and immediately encapsulated in the hydrogels. Comparison of hAC matrix production across different hydrogel formulations were performed using cells from a single donor.

Cell Culture

Cell-laden ClickGels were cultured at 37° C. with 5% $CO_2$ in either expansion media (EM) or chondrogenic media (CM), with media changes every 2-3 days. EM consisted of high glucose DMEM (Invitrogen) supplemented with 10% FBS (Gibco) and 1% penicillin/streptomycin (Corning). CM consisted of high glucose DMEM supplemented with 40 µg/mL L-proline (Sigma), 100 µg/mL sodium pyruvate (Sigma), 1% insulin-transferrin-selenous acid mixture (B&D Bioscience), 100 nM dexamethasone (Sigma) and 10 ng/mL TGF-β3 (R&D systems).

Monitoring Hydrogel Disintegration in EM

The ClickGel disintegration in EM was monitored at 37° C. in a humidified incubator with 5% $CO_2$. As-prepared ClickGels (25 µL, 5% w/v) were placed in 750 µL of EM at 37° C., with change of fresh EM every 2-3 days. The integrity of the ClickGel specimen was monitored daily. The time when the ClickGel completely disintegrated into the aqueous media was recorded as the disintegration time.

Cell Counting Kit-8 (CCK-8) Assay

The viability/proliferation of chondrocytes in each ClickGel formulation (n=3) was examined using CCK-8 assay (Dojindo), which is based on the conversion of a water-soluble tetrazolium salt, to a water-soluble formazan dye upon reduction by dehydrogenases in viable cells. (Han, et al. 2011 *Antimicrob. Agents Chemother.* 55 (10), 4519-4523.) At each time point, the cell-laden ClickGel was incubated with 500-µL 10% v/v CCK-8 reagent in EM for 4 h before the media was transferred to a 96-well plate (100 µL/well, n=3) for absorbance reading at 450 nm using a Multiskan FC microplate photometer (Thermo Scientific). Absorbance of CCK-8 solution incubated in the absence of cell-laden ClickGel was read for background subtraction.

Live/Dead Staining of Encapsulated Chondrocytes

Live (green)/dead (red) staining (Molecular Probes) of the cell-laden 3D constructs was performed with working solutions of 2-µM calcein AM and 1-µM EthD-1 according to manufacturer's instructions. The stained cell-laden ClickGels were mounted on a glass bottom dish and imaged using a TCS SP5 II (Leica) confocal microscope. The composite image was created by overlaying 21 consecutive Z-stack images 5-µm apart.

Histochemical Staining for Glycosaminoglycan (GAG)

Cell-laden ClickGels retrieved from culture were fixed with 10% neutral buffered formalin, serially dehydrated with ethanol and embedded in glycol methacrylate and sectioned into 5-um sections. Mounted sections were stained by toluidine blue to visualize the secreted sulfated GAG (in purple). At least 2 sections, 100 µm apart, were examined for each construct.

Immunofluoresence Staining for Secreted Chondrogenic Matrix Proteins

Cell-laden ClickGels retrieved from culture were fixed by 10% neutral buffered formalin and then washed thrice in in PBS with 1% BSA. Primary antibody against type II collagen (Millipore, 1:200) or type X collagen (eBioscience, 1:200) was added for incubation at 37° C. for at least 1 h with mild agitation. Negative controls were incubated in PBS without primary antibodies. The ClickGels were washed thrice again with PBS (1% BSA). Alexa 488-conjugated goat secondary antibody against mouse (Molecular Probes, 1:200) was added for incubation at 37° C. for 1 h before washes in PBS (0.1% BSA, 3 times) in PBS and staining with DAPI reagent (Invitrogen) according to manufacturer's instructions. The stained 3D hydrogels were first mounted on a glass bottom dish and imaged using a TCS SP5 II (Leica) confocal microscope. They were then bisected to image the interior of the construct. Composite images were created by overlaying 21 Z-stack images 5-μm apart.

Cell Release Studies iMACs were encapsulated in ClickGels formed between 4-armPEG-amide-DBCO and premixed 4-armPEG-ester-azide (0%, 25%, 50%, 75% and 100%) and 4-armPEG-azide. Cell-laden ClickGels were cultured in EM. On days 10, 15 and 30, cells released from the ClickGels and adhered to the culture plates were fixed (10% formalin) and visualized by crystal violet staining, while the cell-laden ClickGels were transferred to a new culture plate for continued culture.

In another subset of experiments, the cell-laden ClickGels were allowed to completely disintegrate within a 5 mL culture tube. The released cells were pelleted at 450×g for 10 min and cultured in EM for 10 days. The pellets were then fixed in 10% formalin, paraffin embedded, sectioned and stained with toluidine blue for GAG or for type II collagen (Millipore, 1:200) by immunohistochemistry with diaminobenzidine (DAB) staining.

Statistical Analysis

One-way or two-way ANOVA with multiple comparisons test was performed as appropriate using Prism (GraphPad, version 7) to determine the statistical significance between different ClickGel formulations (for swelling ratio, compressive modulus, and CCK-8 quantification at each time point), with p value less than 0.05 considered significant.

Applicant's disclosure is described herein in preferred embodiments with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of Applicant's disclosure may be combined in any suitable manner in one or more embodiments. In the description, herein, numerous specific details are recited to provide a thorough understanding of embodiments of the invention. One skilled in the relevant art will recognize, however, that Applicant's composition and/or method may be practiced without one or more of the specific details, or with other methods, components, materials, and so forth. In other instances, well-known structures, materials, or operations are not shown or described in detail to avoid obscuring aspects of the disclosure.

In this specification and the appended claims, the singular forms "a," "an," and "the" include plural reference, unless the context clearly dictates otherwise.

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. Methods recited herein may be carried out in any order that is logically possible, in addition to a particular order disclosed.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

EQUIVALENTS

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance that can be adapted to the practice of this invention in its various embodiments and equivalents thereof.

What is claimed is:

1. A hydrogel comprising a 3-dimensional crosslinking network of a combination of covalent crosslinking (CX) and non-covalent crosslinking (NCX) of hydrophilic branched polymers,

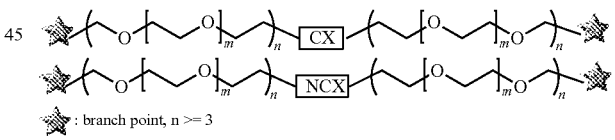

: branch point, n >= 3 wherein
the hydrophilic branched polymers are star-branched with at least 3 arms,
the hydrophilic branched polymers are linked to NCX or CX via one or more labile linkages and one or more stable linkages, wherein the ratio of one or more labile linkages to one or more stable linkages is from about 1:0.2 to about 0.2:1; and
the ratio of CX to NCX is in the range of about 1:10 to about 10:1.

2. The hydrogel of claim 1, wherein the one or more labile linkages are susceptible to hydrolysis.

3. The hydrogel of claim 2, wherein the one or more labile linkages comprise a group selected from the group consisting of ester, carbonate, orthoester, anhydride, and thioester.

4. The hydrogel of claim 1, wherein the one or more stable linkages are resistant to hydrolysis or enzyme cleavage.

5. The hydrogel of claim 4, wherein the one or more stable linkages are selected from the group consisting of amide, C—C, C=C, C≡C, ether, urethane linkages.

6. The hydrogel of claim 1, wherein the hydrophilic polymers are branched polyethylene glycol.

7. The hydrogel of claim 6, wherein the branched polyethylene glycol comprises 4 arms.

8. The hydrogel of claim 1, wherein the covalent cross-linking (CX) is formed by copper-free, strain-promoted azide-alkyne cycloaddition or copper-catalyzed azide-alkyne cycloaddition.

9. The hydrogel of claim 8, wherein the covalent cross-linking (CX) is formed by a click chemistry coupling between:

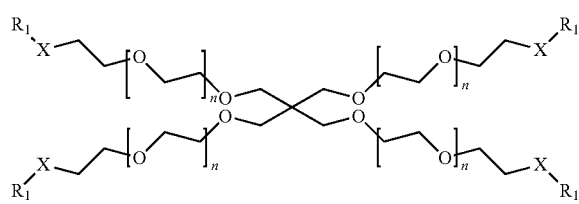

wherein
R$_1$ is a group comprising —N$_3$,
X is selected from ester or carbonate groups or is absent, and
each n is independently an integer from about 1 to about 400; and

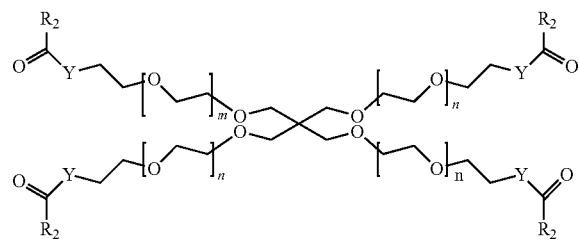

wherein
R$_2$ is

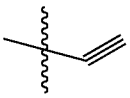 [SMILES: *C#C]

or a group comprising a cyclic or acylic alkyne group,
Y is selected from —NH— and —O— groups or absent, and
each m is independently an integer from about 1 to about 400.

10. The hydrogel of claim 9, wherein R$_2$ is

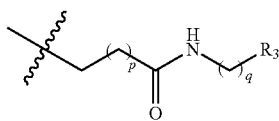

wherein R$_3$ is a group comprising a group comprising a cyclic or acyclic alkyne group, each of p and q is an integer from about 1 to about 6.

11. The hydrogel of claim 1, characterized by one or more of
a compressive stiffness from about 0.2 KPa to about 20 KPa;
a swelling ratio from about 15 to about 150;
a disintegration rate from about 2 days to about 1 year.

12. A hydrogel composition comprising a hydrogel of claim 1 and a biologically active payload encapsulated therein.

13. The hydrogel composition of claim 12, wherein a partial or complete de-crosslinking of the hydrogel partially or completely releases the biologically active payload.

14. A device or implant comprising a hydrogel of claim 1.

* * * * *